United States Patent
Alon et al.

(10) Patent No.: US 11,119,169 B2
(45) Date of Patent: Sep. 14, 2021

(54) MULTI-NUCLEAR ABSOLUTE MR THERMOMETRY

(71) Applicant: NEW YORK UNIVERSITY, New York, NY (US)

(72) Inventors: Leeor Alon, New York, NY (US); Guillaume Madelin, Brooklyn, NY (US); Emilia Silletta, Cordoba (AR); Alexej Jerschow, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/844,840

(22) Filed: Apr. 9, 2020

(65) Prior Publication Data
US 2020/0326397 A1 Oct. 15, 2020

Related U.S. Application Data

(60) Provisional application No. 62/832,167, filed on Apr. 10, 2019.

(51) Int. Cl.
| | | |
|---|---|---|
| G01R 33/48 | (2006.01) |
| G01R 33/56 | (2006.01) |
| G01R 33/44 | (2006.01) |
| A61B 5/055 | (2006.01) |
| G01R 33/421 | (2006.01) |
| G01N 24/08 | (2006.01) |
| G01R 33/485 | (2006.01) |

(52) U.S. Cl.
CPC .......... *G01R 33/4804* (2013.01); *A61B 5/055* (2013.01); *G01N 24/081* (2013.01); *G01R 33/4215* (2013.01); *G01R 33/445* (2013.01); *G01R 33/485* (2013.01); *G01R 33/4806* (2013.01); *G01R 33/5608* (2013.01)

(58) Field of Classification Search
CPC ............ G01R 33/4804; G01R 33/5608; G01R 33/445; G01R 33/4215; G01R 33/4806; G01R 33/485; A61B 5/055; G01N 24/081
See application file for complete search history.

(56) References Cited

U.S. PATENT DOCUMENTS

| | | | | |
|---|---|---|---|---|
| 5,378,987 A * | 1/1995 | Ishihara | ............... | G01R 33/485 |
| | | | | 324/315 |
| 6,194,899 B1 * | 2/2001 | Ishihara | ............. | G01R 33/4804 |
| | | | | 324/315 |
| 2012/0071746 A1 * | 3/2012 | Vortman | ............ | G01R 33/4804 |
| | | | | 600/411 |
| 2016/0273970 A1 * | 9/2016 | Alon | ..................... | G01K 11/006 |

OTHER PUBLICATIONS

De Poorter, "Noninvasive MRI thermometry with the proton resonance frequency method: Study of susceptibility effects," Magnetic Resonance in Medicine 34(3), pp. 359-367 (1995).

(Continued)

*Primary Examiner* — G. M. A Hyder
(74) *Attorney, Agent, or Firm* — Foley & Lardner LLP

(57) ABSTRACT

System and methods that reconstruct absolute temperature using a multi-nuclear approach. Specifically, the methods and systems utilize independent NMR/MRI information provided by the precession frequency of two different nuclei to reconstruct a map of the absolute temperature.

20 Claims, 19 Drawing Sheets

(56) References Cited

OTHER PUBLICATIONS

Ng, et al., "Statistical analysis of healthy and malignant breast thermography," Journal of Medical Engineering & Technology 25(6), pp. 253-263 (2001).
Rigotti, et al., "Global N-Acetylaspartate Declines Even in Benign Multiple Sclerosis," American Journal of Neuroradiology 32(1), pp. 204-209 (2011).
Seagale, "The Temperature of Acutely Inflamed Peripheral Tissue," Journal of Experimental Medicine 29(3), pp. 235-249 (1919).
Wang, et al., "Brain temperature and its fundamental properties: a review for clinical neuroscientists," Frontiers in Neuroscience 8, 307, 17 pages (2014).

* cited by examiner

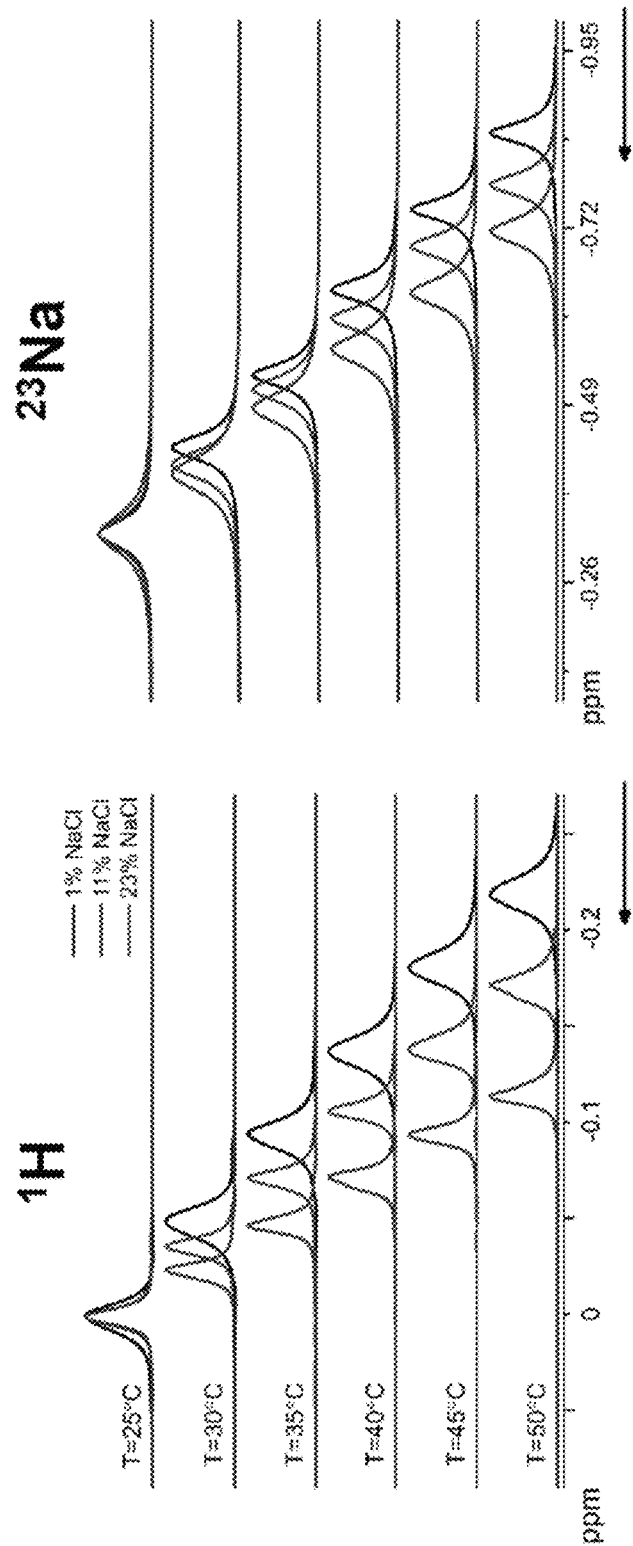

FIG. 2G
FIG. 2H
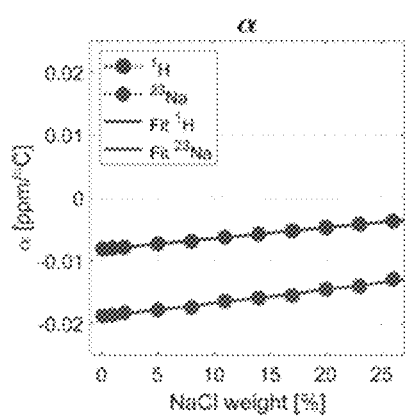
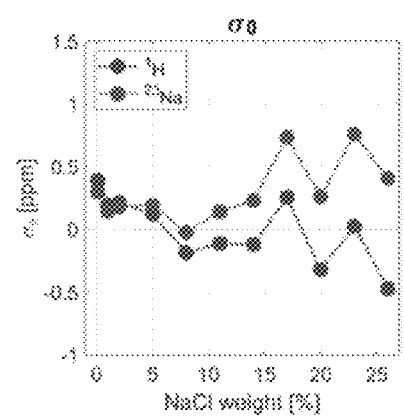
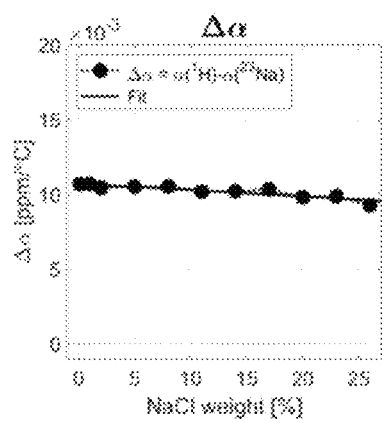
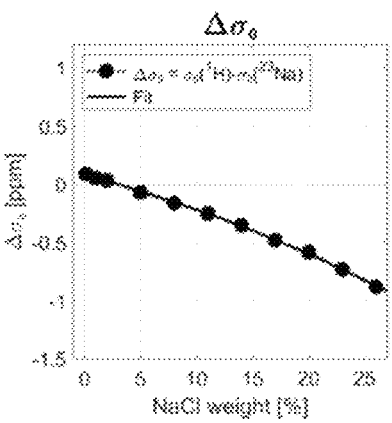
FIG. 2I
FIG. 2J

FIG. 3G
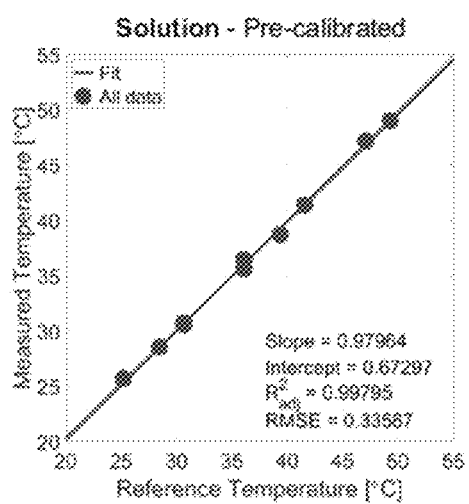
FIG. 3I
FIG. 3H
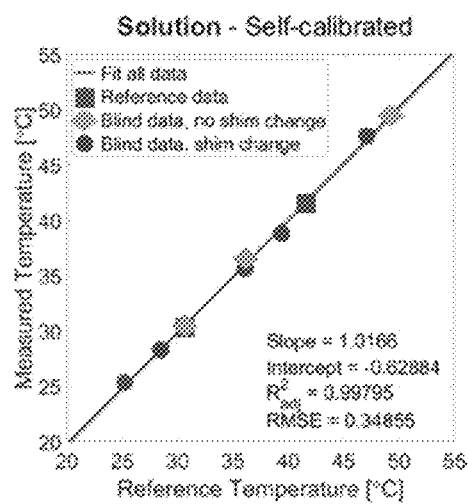
FIG. 3J
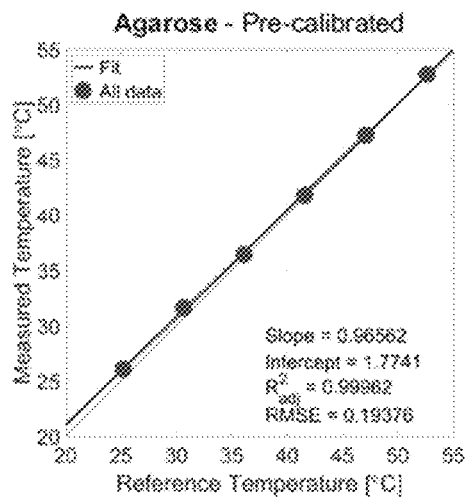
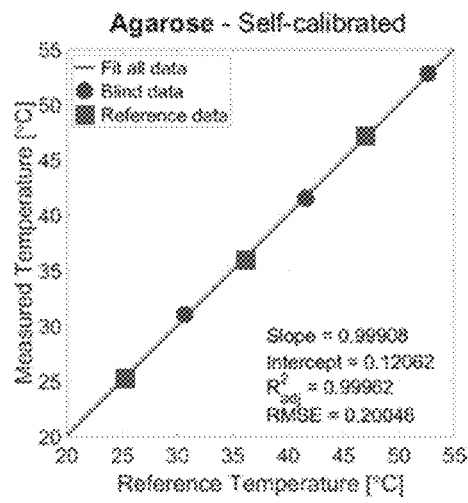

| [NaCl] (%wt) | α (ppm/°C) | 95% CB for α | $\omega_0$ (ppm) | 95% CB for $\omega_0$ | $R^2_{adj}$ | RMSE |
|---|---|---|---|---|---|---|
| $^1$H | | | | | | |
| 0.1 | -0.008140 | (-0.008575,-0.007749) | 0.3878 | (0.3721,0.4051) | 0.99863 | 0.00310 |
| 1 | -0.007981 | (-0.008452,-0.007467) | 0.1943 | (0.1739,0.2133) | 0.99810 | 0.00357 |
| 2 | -0.007882 | (-0.008271,-0.007382) | 0.2111 | (0.1915,0.2271) | 0.99779 | 0.00380 |
| 5 | -0.007351 | (-0.007730,-0.006855) | 0.1215 | (0.1019,0.1368) | 0.99768 | 0.00364 |
| 8 | -0.006942 | (-0.007342,-0.006576) | -0.1868 | (-0.2015,-0.1709) | 0.99839 | 0.00286 |
| 11 | -0.006271 | (-0.006487,-0.006050) | -0.1125 | (-0.1213,-0.1038) | 0.99887 | 0.00216 |
| 14 | -0.005769 | (-0.006041,-0.005451) | -0.1235 | (-0.1363,-0.1127) | 0.99785 | 0.00274 |
| 17 | -0.005257 | (-0.005507,-0.005008) | 0.2543 | (0.2442,0.2641) | 0.99835 | 0.00219 |
| 20 | -0.004729 | (-0.004958,-0.004490) | -0.3234 | (-0.3330,-0.3143) | 0.99840 | 0.00194 |
| 23 | -0.004199 | (-0.004528,-0.003952) | 0.0237 | (0.0137,0.0367) | 0.99800 | 0.00193 |
| 26 | -0.003703 | (-0.003924,-0.003423) | -0.4735 | (-0.4846,-0.4646) | 0.99695 | 0.00210 |
| $^{23}$Na | | | | | | |
| 0.1 | -0.018824 | (-0.019000,-0.018580) | 0.2972 | (0.2973,0.3041) | 0.99987 | 0.00221 |
| 1 | -0.018681 | (-0.019180,-0.018150) | 0.1398 | (0.1189,0.1599) | 0.99945 | 0.00449 |
| 2 | -0.018311 | (-0.018800,-0.017850) | 0.1777 | (0.1590,0.1970) | 0.99958 | 0.00385 |
| 5 | -0.017871 | (-0.018270,-0.017430) | 0.1899 | (0.1724,0.2057) | 0.99970 | 0.00319 |
| 8 | -0.017464 | (-0.018300,-0.016640) | -0.0257 | (-0.0587,0.0078) | 0.99835 | 0.00729 |
| 11 | -0.016463 | (-0.017110,-0.015770) | 0.1382 | (0.1107,0.1643) | 0.99912 | 0.00501 |
| 14 | -0.015986 | (-0.016640,-0.015320) | 0.2288 | (0.2018,0.2544) | 0.99874 | 0.00584 |
| 17 | -0.015593 | (-0.016100,-0.015130) | 0.7333 | (0.7150,0.7537) | 0.99938 | 0.00398 |
| 20 | -0.014532 | (-0.014980,-0.014110) | 0.2600 | (0.2433,0.2784) | 0.99944 | 0.00352 |
| 23 | -0.014079 | (-0.014500,-0.013630) | 0.7565 | (0.7383,0.7730) | 0.99951 | 0.00321 |
| 26 | -0.012970 | (-0.013550,-0.012400) | 0.4063 | (0.3839,0.4297) | 0.99871 | 0.00478 |

Abbreviations: CB = Confidence Bounds; RMSE = Root Mean Square Error; $R^2_{adj}$ = adjusted $R^2$.

FIG. 12

| Fit parameters | α (ppm/°C) for ¹H | α (ppm/°C) for ²³Na | Δα (ppm/°C) | Δα₀ (ppm) |
|---|---|---|---|---|
| a | 0.000172 | 0.000215 | -4.303e-05 | -0.0004218 |
| 95% CB for a | (0.000168, 0.000177) | (0.000199, 0.000232) | (-5.735×10⁻⁵, -2.87×10⁻⁵) | (-0.0005425, -0.000301) |
| b | -0.00818183 | -0.01892 | 0.01073 | -0.02573 |
| 95% CB for b | (-0.008248, -0.008117) | (-0.01915, -0.01868) | (0.01053, 0.01094) | (-0.02884, -0.02262) |
| c | | | | 0.0829 |
| 95% CB for c | | | | (0.06756, 0.09823) |
| R²ₐdⱼ | 0.99966 | 0.98882 | 0.81874 | 0.99898 |
| RMSE | 5.77×10⁻⁵ | 2.09×10⁻⁴ | 1.83×10⁻⁴ | 0.01056 |

Abbreviations: CB = Confidence Bounds; RMSE = Root Mean Square Error; R²ₐdⱼ = adjusted R².

FIG. 13

MULTI-NUCLEAR ABSOLUTE MR THERMOMETRY

CROSS-REFERENCE TO RELATED APPLICATIONS

The present application claims the benefit of and priority to U.S. Provisional Application No. 62/832,167, filed Apr. 10, 2019, which is hereby incorporated by reference in its entirety.

TECHNICAL FIELD

The present disclosure relates generally to methods and systems to reconstruct absolute temperature using a multi-nuclear magnetic resonance (MR) approach.

BACKGROUND

A unique feature of magnetic resonance imaging (MM) is its contrast-sensitivity to temperature changes. For water, MR parameters such as the longitudinal relaxation time (T1), transverse relaxation time (T2), proton density (M0), diffusion coefficient (D) and chemical shift (CS) are all temperature-dependent. The chemical shift of protons, also known as the "proton resonance frequency (PRF) shift" phenomenon, has been shown to have the greatest sensitivity to temperature fluctuations. This temperature effect was first discovered in 1966 by Hindman, when conducting nuclear magnetic resonance (NMR) experiments on intermolecular forces and hydrogen bond formation. The technique was adapted to MRI by Ishihara et al. and De Poorter in 1995 using MR phase measurements to measure relative temperature changes, but not absolute temperature. Phase imaging techniques are currently the gold standard for mapping thermal changes in a great number of applications including: monitoring of in vivo temperature change due to high intensity focused ultrasound (HIFU), radiofrequency (RF) hyperthermia treatment, assessment of RF power deposition from antennas, and more.

The PRF method relies on the subtraction of pre- and post-heating phase images, or observing frequency changes pre- and post-heating. However, non-thermal local $B_0$ changes such as patient movement, magnetic field drift and other physiological noise (e.g., flow), greatly limit the applicability of the PRF method in vivo. Currently, PRF thermometry is mainly restricted to experiments with large thermal gradients (>2° C.) or phantom studies with minimal $B_0$ drift throughout the experiment. Several groups have attempted to measure temperature change using a single measurement by utilizing priors relating to the distribution of temperature change induced in the body. For example, in the case of HIFU, the heating pattern is localized (<1 cm in diameter). As a result, the phase change induced by any $B_0$ changes (such as from breathing motion) can be distributed over the entire field-of-view (FOV) of the image. A polynomial fit can be used to estimate the background $B_0$ change and subtract the phase due to the "background $B_0$ field" from the measured phase image in order to estimate the temperature change in the focal spot. While this approach is used in applications where the heating is strong and focused, it is not practical for applications where the thermal changes are distributed in the body.

In order to avoid errors induced in frequency or phase measurements and properly reconstruct absolute temperature, an internal frequency reference (at each voxel) may be necessary. From that reference, the water chemical shift can be determined. Internally referenced measurements of temperature are used in NMR to monitor absolute temperature by measuring the chemical shift between two or more temperature-dependent peaks such as the measurement of the chemical shift between methyl and hydroxyl groups, in methanol or methylene and hydroxyl groups in ethylene glycol. Experiments where the frequency difference between two independent peaks may be robust against instabilities in $B_0$ because changes in macroscopic $B_0$ at each location can shift the frequency of the independent peaks equally. While methanol and glycol can be used in in situ NMR experiments, these molecules are not ubiquitous in the human body and cannot be used in vivo. Internally referenced chemical shifts have been investigated in the brain in vivo using the amide proton in N-acetylaspartate (NAA) and water peaks, showing an estimation error of temperature of ±0.4° C. However, due to the low concentrations of NAA in vivo, ~10 mM in the human brain and less in other organs, challenges associated with water suppression and imaging time required to attain adequate signal-to-noise (SNR), absolute thermometry via imaging of the NAA peak using chemical shift imaging (CSI) remains challenging for routine clinical scanning.

Fat is often used as a reference peak, which is separated from water by approximately 3.5 ppm. Fat contains relatively few hydrogen bonds, and its PRF thermal coefficient is mainly dictated by the volume-magnetic susceptibility which is small compared to that of water. Studies have therefore shown that fat in surrounding tissues can be used to estimate the background $B_0$ changes, and information provided by the fat peaks has been used to improve the temperature change reconstruction. Nonetheless, fat is absent from most organs and does not provide a sensitive enough internal reference.

With these challenges in mind, current state-of-the-art PRF thermometry techniques are limited in vivo where the temperature change is relatively large and/or where the spatial-temporal $B_0$ changes are small relative to the $B_0$ changes induced due to thermal changes.

SUMMARY

Non-invasive measurement of absolute temperature is important for the characterization of various pathologies and for evaluation of thermal dose during interventional procedures. The proton (hydrogen nucleus) magnetic resonance (MR) frequency shift method can be used to map relative temperature changes. However, spatiotemporal variations in the main magnetic field and the lack of local internal frequency reference challenge the determination of absolute temperature. In some embodiments, a multi-nuclear method for absolute MR thermometry is disclosed, based on two endogenous types of molecules in biological tissues, water and sodium ions $Na^+$, as well as a general framework for absolute MR thermometry that can be used with any pair of nuclei. The hydrogen and sodium nuclei exhibit a unique and distinct characteristic frequency dependence with temperature and with electrolyte concentration. A one-to-one mapping between the precession frequency difference of the two nuclei and absolute temperature is demonstrated. Proof-of-concept experiments were conducted in aqueous solutions with different NaCl concentrations, in agarose gel samples, and freshly excised ex vivo mouse tissues. One-dimensional chemical shift imaging experiments also demonstrated agreement with infrared measurements.

Magnetic resonance imaging (MRI) can be a valuable diagnostic tool for visualization of subtle pathologies with millimeter resolution. MR techniques can be used to measure temperature changes in vivo. MR contrast mechanisms can vary with temperature change. The proton ($^1$H) resonance frequency (PRF) method can have the highest sensitivity to thermal change in most tissues. The PRF method can be used for mapping thermal changes in interventional applications, such as high-intensity focused ultrasound (HIFU), radiofrequency (RF) hyperthermia, RF ablation, and RF power deposition from wireless devices.

The PRF method can rely on the subtraction of pre- and post-exposure phase images, or on the local determination of the frequency shift of protons with MR spectroscopy (MRS), to calculate temperature change due to exposure conditions, knowing that the chemical shift temperature dependence of proton is approximately –0.01 ppm/° C. in human tissues. However, non-thermal $B_0$ changes, such as those due to movement, magnet field $B_0$ drift; flow, or shim changes, can greatly limit the applicability of the PRF method. PRF thermometry can be restricted to experiments with large thermal gradients or phantom studies with minimal $B_0$ drift throughout the experiment. Furthermore, PRF methodologies may not be capable of reconstruction of absolute temperature in tissues, because an internal frequency reference (in each voxel) is required. Knowledge of the absolute temperature in tissues can be important due to the correlation of many pathologies with thermal disruption and is fundamental for quantification of thermal dose during interventional procedures. In NMR experiments, internally referenced measurements of absolute temperature can be used to monitor the temperature of samples by measuring the chemical shift between two or more temperature-dependent peaks such as between the OH and $CH_2$ groups in ethylene glycol. Internally referenced experiments are robust against instabilities of $B_0$ because changes in macroscopic $B_0$ equally shift the independent peaks, enabling the reconstruction of absolute temperature. In the brain, the amide proton in N-acetylaspartate (NAA) peak can be utilized as a temperature-independent reference. However, due to the low concentration of NAA in the brain (~10 mmol/L), challenges associated with water suppression, pH-dependent separation of the NAA-water peaks, and imaging time required to obtain adequate signal-to-noise ratio (SNR), absolute thermometry via imaging of the NAA peak remain.

In some embodiments, a computer-implemented machine for reconstruction of absolute temperature of a sample includes a processor; and a tangible computer-readable medium operatively connected to the processor and including computer code configured to: determine a frequency for a first nucleus at, at least, one location in the sample; determine a second frequency for the second nucleus at the at least one location in the sample; normalize the frequency for the first nucleus with a first intramolecular shielding constant to obtain normalized frequency information for the first nucleus; normalize the frequency for the second nucleus with a second intramolecular shielding constant to obtain normalized frequency information for the second nucleus; and determine an absolute temperature of the sample based on a difference between the normalized frequency information for the first nucleus and the normalized frequency information for the second nucleus, wherein the first nucleus and the second nucleus are different elements.

In another embodiment, a method for reconstruction of absolute temperature of a sample includes determining a frequency for a first nucleus at, at least, one location in the sample; determining a frequency for a second nucleus at the at least one location in the sample; normalizing the frequency for the first nucleus with a first intramolecular shielding constant to obtain normalized frequency information for the first nucleus; normalizing the frequency for the second nucleus with a second intramolecular shielding constant to obtain normalized frequency information for the second nucleus; and determining an absolute temperature of the sample based on a difference between the normalized frequency information for the first nucleus and the normalized frequency information for the second nucleus, wherein the first nucleus and the second nucleus are different elements.

In a further embodiment, a method for reconstruction of absolute temperature of a sample includes acquiring spectra directly from MR spectroscopy from a first nucleus and a second nucleus different from the first element, the first nucleus and the second nucleus being present in the sample; reconstructing frequency information for the first nucleus and frequency information for the second nucleus; and determining the absolute temperature of the sample based on a difference between the frequency information for the first nucleus and the frequency information for the second nucleus, wherein the first nucleus and the second nucleus are different elements such as selected from the group consisting of $^1$H, $^{23}$Na, $^{31}$P, $^{35}$Cl, $^{17}$O, $^6$Li, or $^{39}$K.

In an additional embodiment, a method for reconstruction of absolute temperature of a sample includes acquiring phase MR imaging using a first nucleus of a first element and a second nucleus of a second element different from the first element, the first nucleus and the second nucleus being present in the sample; reconstructing phase information for each of the first nucleus and the second nucleus; indirectly obtaining frequency information for each of the first nucleus and the second nucleus based on the reconstructed phase information for each of the first nucleus and the second nucleus; and determining the absolute temperature of the tissue or the organ based on a difference between the frequency information for the first nucleus and the frequency information for the second nucleus, wherein the first nucleus and the second nucleus are different elements such as selected from the group consisting of $^1$H, $^{23}$Na, $^{31}$P, $^{35}$Cl, $^{17}$O, $^6$Li, $^7$Li, or $^{39}$K.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through the use of the accompanying drawings.

FIG. 1A is a graph showing a frequency of a hydrogen/proton ($^1$H) nucleus relative to a reference peak at a predetermined temperature, according to an embodiment.

FIG. 1B is another graph showing a frequency of a sodium ($^{23}$Na) nucleus relative to a reference peak at a predetermined temperature, according to an embodiment.

FIGS. 2G-2J show the results of the linear fitting of the frequency shift of $^1$H and sodium $^{23}$Na versus temperature for 11 samples, according to an embodiment.

FIGS. 3G-3J show absolute temperature measurements in solutions and agarose, according to an embodiment.

FIG. 12 shows linear fits of frequency shift f vs. temperature T: $f=\alpha T+\sigma_0$, according to an embodiment.

FIG. 13 shows fitting parameters for $\alpha$, $\Delta\alpha$, $\Delta\sigma_0$ versus NaCl concentrations in weight % ($C_{\%\ wt}$), according to an embodiment.

Figure 2A:
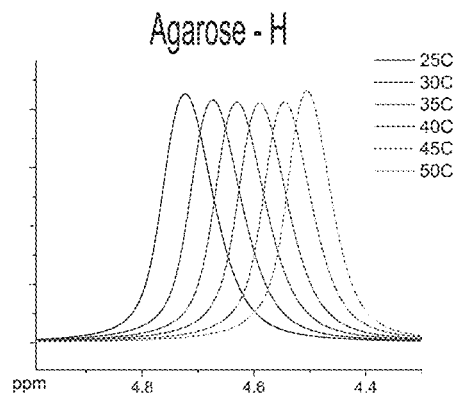
FIG. 2A shows hydrogen/proton ($^1$H) frequency shifts with temperature for an Agarose sample, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to methods and systems to reconstruct absolute temperature and/or $B_0$ using a multi-nuclear approach. Specifically, the methods and systems utilize independent NMR/MRI information provided by the precession frequency of two or more different nuclei (e.g., two nuclei, three nuclei, four nuclei, five nuclei, etc.) to reconstruct a map of the absolute temperature. One advantage of using nuclei other nuclei than $^1$H, such as $^{23}$Na, $^{31}$P, $^{35}$Cl, $^{17}$O, $^6$Li, $^7$Li, or $^{39}$K, is that the signal is obtained mostly from the aqueous phase where sodium is fully solvated. In this case, a single NMR peak is observed in contrast to proton NMR, where more complex NMR interactions are present. As a result, absolute thermometry can be enabled with the use of a multi-nuclear NMR approach.

A multinuclear method for absolute MR thermometry is disclosed, based on two endogenous types of molecules in biological tissues, water and sodium ions Na$^+$, as well as a general framework for absolute MR thermometry that can be used with any pair of nuclei. $^{23}$Na nuclei exhibit an NMR frequency shift dependency with temperature that is roughly twice that of the $^1$H nuclei. Thus, measuring the difference of NMR frequencies of the $^{23}$Na and $^1$H nuclei can provide a one-to-one mapping with temperature, allowing absolute temperature reconstruction with reduced sensitivity to macroscopic B$_0$ inhomogeneities (or random shim variations), and without the need of a fixed temperature-independent reference peak. Proof-of-concept experiments were conducted in aqueous solutions with different NaCl concentrations, in agarose gel samples, and in freshly-excised ex vivo mouse tissues. One-dimensional chemical shift imaging (CSI) was also performed for two steady-state temperature regimes.

As mentioned, MR thermometry is challenged by: the determination of absolute temperature changes in vivo and the location-specific changes in the B$_0$ distribution due to physiological noise, or frequency changes induced by hardware instabilities that are significantly greater than the frequency differences induced by thermal changes. In this work, the frequency information of two independent nuclei is obtained (e.g. protons and sodium) and used to reconstruct absolute temperature while overcoming errors caused by non-thermal B$_0$ changes. Below is a mathematical description of the proposed approach.

The Larmor frequency, $f^N$ of the magnetic moment of a nucleus N is determined by the magnetic field, B$_{nuc}$ that the nucleus experiences and the gyromagnetic ratio, $\gamma^N$, of a nucleus of interest. B$_{nuc}$ is the result of a shielding constant, $\sigma^N$, altering the macroscopic magnetic field, B$_0$, according to:

$$f^N = \frac{\gamma}{2\pi} B_{nuc} = \frac{\gamma^N}{2\pi}(1-\sigma^N)B_0. \qquad [1]$$

The shielding constant is expressed as:

$$\sigma^N = \sigma_i^N + \sigma_X^N + \sigma_e^N \qquad [2]$$

where $\sigma_i^N$ is the intramolecular shielding constant, $\sigma_e^N$ is the intermolecular electric screening effect, and $\sigma_X^N$ is the volume magnetic susceptibility screening effect. Both $\sigma_X^N$ and $\sigma_e^N$ change with temperature T. The precession frequency can thus be expressed as:

$$f^N(T) = \frac{\gamma^N}{2\pi}[1-\sigma_i^N-\sigma_X^N(T)-\sigma_e^N(T)]B_0 \qquad [3]$$

By defining $$f_0^N = \frac{\gamma}{2\pi}B_0,$$

the frequency shift $\delta f^N(T)$ of a nucleus N, in parts-per-million (ppm) can be calculated as:

$$\delta f^N(T) = \frac{f_0^N - f^N(T)}{f_0^N} \qquad [4]$$

This can be expressed as the sum of a temperature-independent component and a temperature-dependent component:

$$\delta f^N(T) = [\sigma_i^N] + [\sigma_X^N(T) + \sigma_e^N(T)] \qquad [5]$$

Since the temperature dependency of $\sigma_X^N$ and $\sigma_e^N$ is linear with temperature, the susceptibility and electric shielding can be written as:

$$\sigma_X^N(T) = \sigma_{X_0}^N + \alpha_X^N \cdot T \qquad [6a]$$

$$\sigma_e^N(T) = \sigma_{e_0}^N + \alpha_e^N \cdot T \qquad [6b]$$

Equations [6a] and [6b] can be combined such that the nucleus' frequency shift is rewritten as a constant $\sigma_0^N$ (in ppm) and a frequency shift thermal coefficient $\alpha^N$ (in ppm/°C.):

$$\delta f^N(T) = \sigma_0^N + \alpha^N \cdot T \qquad [7]$$

With:

$$\sigma_0^N = \sigma_i^N + \sigma_{X_0}^N + \sigma_{e_0}^N \qquad [8a]$$

$$\alpha^N = \alpha_X^N + \alpha_e^N \qquad [8b]$$

Measurement of Relative Temperature Change

The frequency shift thermal coefficient $\alpha^N$ can be calibrated for a specific nucleus (e.g., $^1$H) and a sample of interest. Since $\delta f^N$ can vary with local B$_0$ fluctuations (shim, motion, and field drift), and the component $\sigma_0^N$ is generally unknown and can vary due to different electronic and susceptibility shieldings, absolute temperature cannot be calculated using Eq. [7]. This equation can, however, be used to measure relative temperature changes using nucleus N=$^1$H MRS or MM (PRF method) and a calibrated value $\alpha^N \sim -0.01$ ppm/°C. in human tissues. By subtracting the frequency shifts measured at two different times (e.g., before and after heating), the effect of $\sigma_0^N$ is canceled and relative temperature changes are calculated as:

$$\Delta T = T_1 - T_2 = \frac{\delta f^N(T_1) - \delta f^N(T_2)}{\alpha^N} \qquad [9]$$

Measurement of Absolute Temperature

Absolute temperature can be derived from Eq. [7] by detecting the frequency shift of two nuclei within the same sample or voxel (in case of localized MRS or MM), where the difference between their respective frequency shift thermal coefficients $\alpha$ and constants $\sigma_0$ are well-known theoretically or calibrated experimentally. Using the following definitions for two nuclei N≡A, B (which can even be of the same species, but from a different molecule or local environment)

$$\Delta f(T) = \delta f^A(T) - \delta f^B(T) \qquad [10a]$$

$$\Delta \sigma_0 = \sigma_0^A - \sigma_0^B \qquad [10b]$$

$$\Delta \alpha = \alpha^A - \alpha^B \neq 0 \qquad [10c]$$

The frequency shift difference between the two nuclei can thus be written $$\Delta f(T) = \Delta \sigma_0 + \Delta \alpha(T) \qquad [11]$$

Upon calibration of $\Delta\sigma_0$ and $\Delta\alpha$ for the two nuclei and samples of interest (fluid, tissue), absolute temperature of the sample can be calculated as follows:

$$T = \frac{\Delta f(T) - \Delta \sigma_0}{\Delta \alpha} \quad [12]$$

The absolute temperature can be measured using two different nuclei, $^1H$ and $^{23}Na$, which both exhibit a unique frequency dependency with temperature. The two nuclei are conjointly present in a hydrated sample (and thus experience the same local $B_0$ variations, as well as similar electronic and susceptibility environments), as sodium ions $Na^+$ are mostly present in hydrated state in the water compartment of the body or a sample of interest. The NMR frequency shifts of $^1H$ (hydrogen from water) and $^{23}Na$ (from ion $Na^+$) nuclei at different temperatures in solutions with different NaCl concentrations are measured, as well as in agarose gel and in ex vivo mouse tissue samples, in order to measure their respective linear dependence with temperature and calibrate their respective $\Delta\alpha$ and $\Delta\sigma_0$. These two latter values can be used to calculate the absolute temperature of the samples in blind experiments, where the temperature of the sample was known from the spectrometer sensor, but not used for the calibration of $\Delta\alpha$ and $\Delta\sigma_0$.

NMR Experiments

Experiments were carried out on an 11.7 T NMR Bruker Avance I spectrometer (Bruker BioSpin) operating at 500.19 MHz for $^1H$, and 132.3 MHz for $^{23}Na$, using a 5 mm double resonance broadband probe. The test tubes with different samples under investigation (aqueous solutions with different NaCl concentrations, agarose gel, ex vivo tissues) were placed inside the spectrometer where the sample temperature could be controlled using gas flow and a temperature sensor providing a precise, stable and reliable temperature regulation. After each desired temperature was reached, a standard free induction decay (FID) pulse sequence was used with a 90° pulse. The duration of the pulse is 11 and 9 µs for $^1H$ and $^{23}Na$, respectively, and 8 averages were used with TR=15 s for 41, and 0.5 s for $^{23}Na$, dwell time dw=100 µs, spectral width sw=5 kHz, 16,384 data points per spectrum. Complex FIDs were acquired in digital quadrature detection (DQD) mode, a simultaneous acquisition mode in Bruker systems resuming in $$sw = \frac{1}{2dw}.$$

All experiments were performed with the following exact spectrometer reference frequencies:

$$f_0^H = 500.2031765 \text{ MHz},$$

$$f_0^{Na} = 132.3120951 \text{ MHz} \left(\text{fixed ratio } \frac{f_0^H}{f_0^{Na}} = 3.7804796\right).$$

Sample Preparation

Solution samples with 11 different NaCl concentrations (C=0.1, 1, 2, 5, 8, 11, 14, 17, 20, 23, 26% weight) were prepared by mixing x mg of NaCl in (y−x) mg of deionized water in a beaker (with x=0.1 mg and y=100 mg for the sample C=0.1% weight, and with x=0.1, 0.2, 0.5, 0.8, 1.1, 1.4, 1.7, 2.0, 2.3, 2.6 mg and y=10 mg for the other samples), and transferred to 5 mm NMR tubes (sample volume=0.5 mL). All mass measurements were performed on a Mettler Toledo ME204E balance with a resolution of 0.1 mg. The solution at 26% weight corresponds to NaCl saturation in water. Corresponding NaCl concentrations in mol/L and uncertainties on the measurements can be calculated. The results of the calculated NaCl concentrations in mol/L with uncertainties are presented in Table 1. A gel was prepared by mixing 2% w/v of agarose with 1% w/v NaCl in deionized water. The gel mixture was incrementally heated in a microwave to fully dissolve the agarose. The solution was poured into a 5 mm NMR tube forming a uniform, homogeneous gel upon cooling.

TABLE 1

NaCl concentration calibration

| | [NaCl] | | | | | | | | | | |
|---|---|---|---|---|---|---|---|---|---|---|---|
| $C_{\% wt}$(% wt) | 0.1 | 1 | 2 | 5 | 8 | 11 | 14 | 17 | 20 | 23 | 26 |
| $\sigma_{C_{\% wt}}$(% wt) | ±0.05 | ±0.5 | ±0.5 | ±0.5 | ±0.5 | ±0.5 | ±0.5 | ±0.5 | ±0.5 | ±0.5 | ±0.5 |
| $C_{mol/L}$(mol/L) | 0.017 | 0.172 | 0.346 | 0.885 | 1.446 | 2.030 | 2.637 | 3.269 | 3.924 | 4.605 | 5.311 |
| $\sigma_{C_{mol/L}}$(mol/L) | ±0.008 | ±0.087 | ±0.088 | ±0.091 | ±0.095 | ±0.099 | ±0.103 | ±0.107 | ±0.111 | ±0.115 | ±0.120 |

Tissue Samples

Four tissue samples (brain, kidney, liver, and muscle) were obtained from two female mice whose weights were 22.2 g and 25 g.

Data Processing

Figure 10:
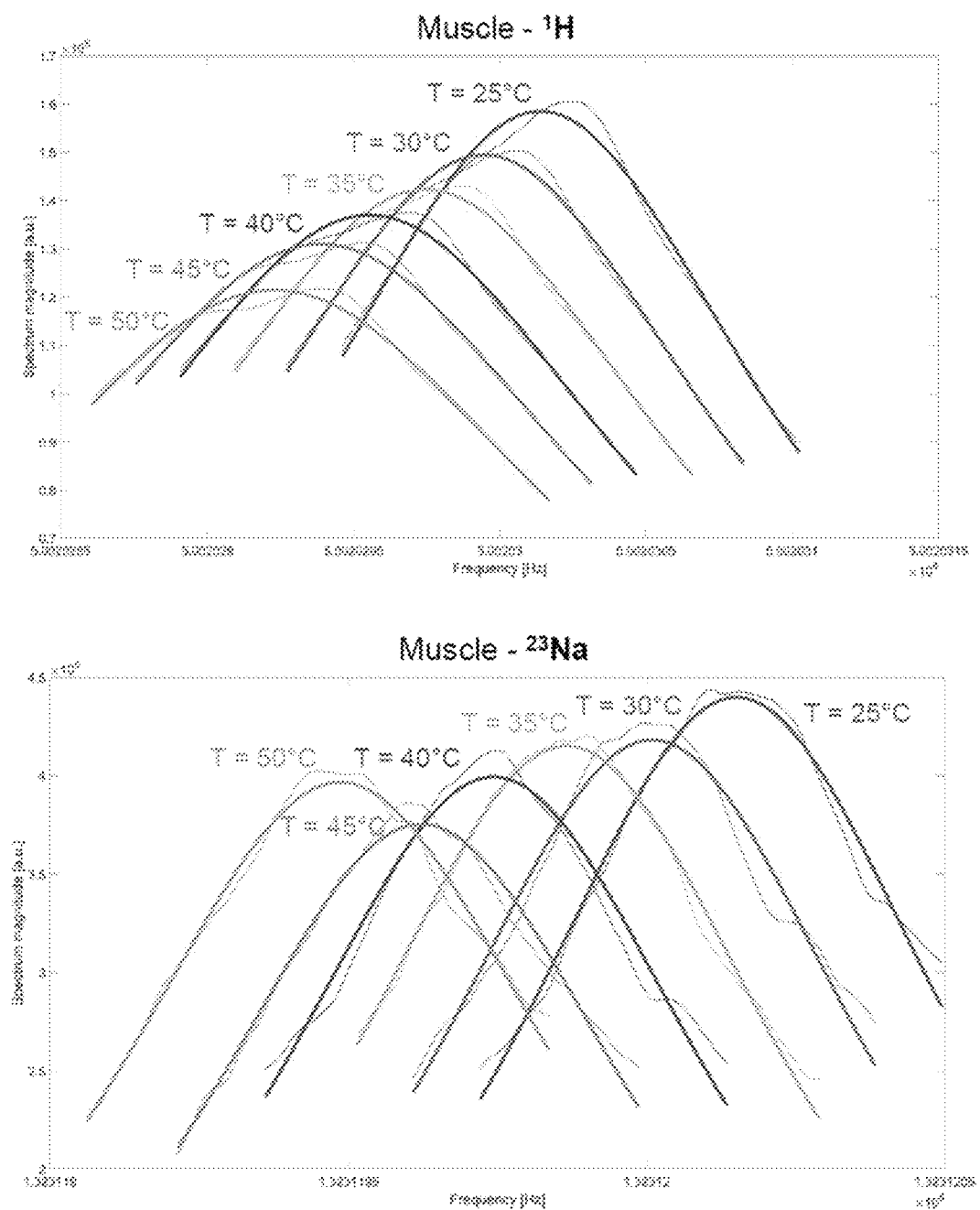
FIG. 10 shows examples of single Lorentzian fitting of 256+1 data points around the maximum of the $^1$H and $^{23}$Na spectra at different temperatures for the muscle tissue sample, according to an embodiment.
Figure 11:
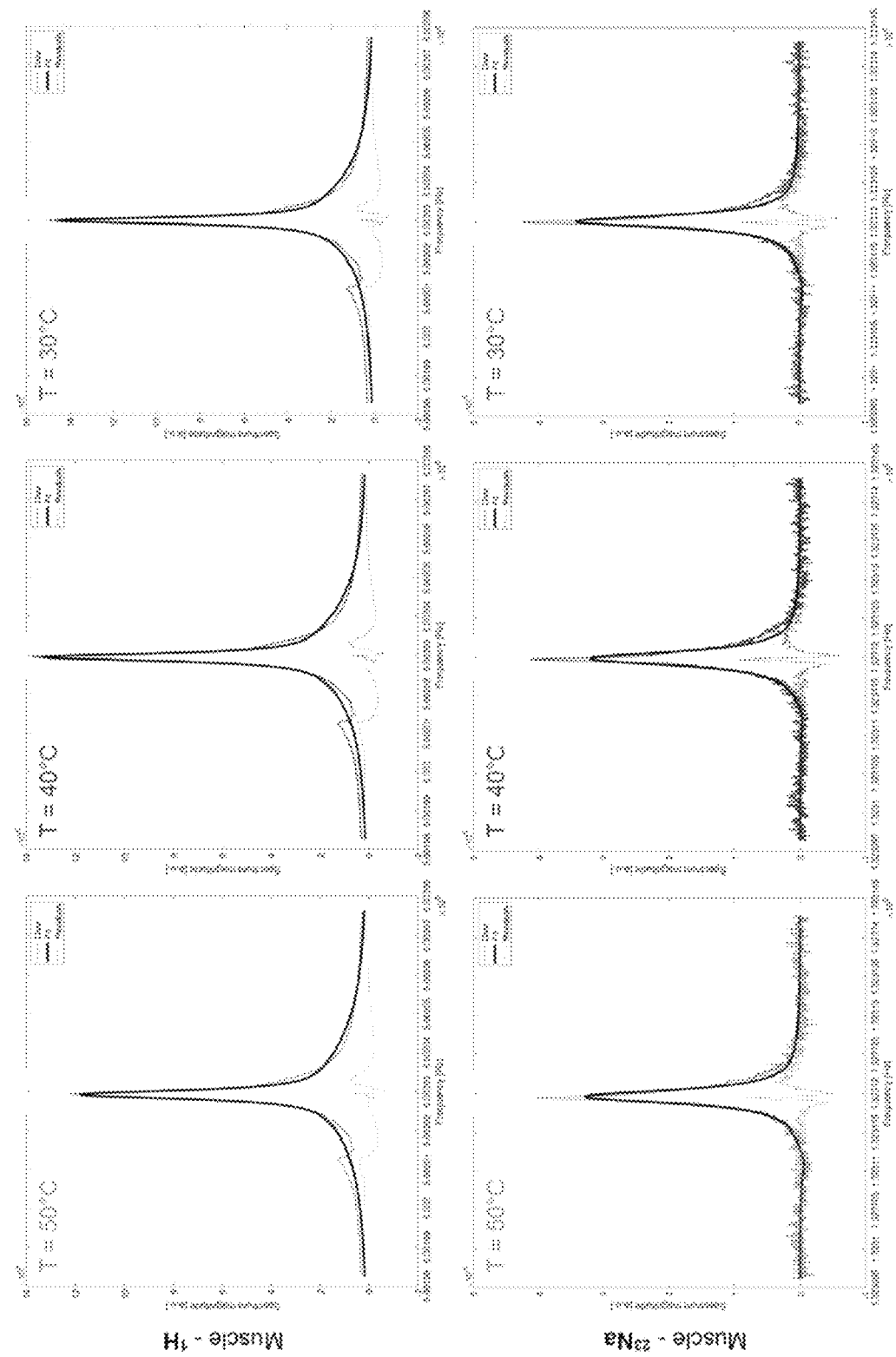
FIG. 11 shows examples of bi-Lorentzian fitting of full $^1$H and $^{23}$Na spectra at 3 different temperatures for the muscle tissue, according to an embodiment.

The frequency shifts of the $^1H$ and $^{23}Na$ signals were detected at each temperature by tracking the position of the maximum of peak of their NMR spectrum: (1) The maximum of each magnitude spectrum was detected and 256 data points around this maximum were selected (128 points on each side); (2) the 257 data points (including the maximum point) were then fitted by a Lorentzian function; (3) the maximum of the Lorentzian fit was detected and its corresponding frequency was selected as the frequency shift of interest for this particular spectrum. Although this maximum-of-fit detection method was not necessary for solution and gel samples, it proved to slightly improve the robustness of the frequency shift detection in tissue samples, particularly when SNR was low or when the peaks were distorted due to local susceptibility inhomogeneities. Examples of fitting results for both $^1H$ and $^{23}Na$ spectra from the muscle sample at different temperatures are shown in FIG. 10. For comparison, three examples of fits of the whole spectra in the muscle sample using a bi-Lorentzian function, at three different temperatures are shown in FIG. 11. Due to variations in spectra shapes caused by both global and local magnetic field inhomogeneities in our biological samples, the (256+1)-point fitting method used to track the frequency shift as described above was more robust compared to whole spectra fitting. Data processing was performed in Matlab (The MathWorks Inc., Natick, Mass., USA).

Measurements of $\alpha$ and $\sigma_0$ for $^1H$ and $^{23}Na$ in Solutions

The frequency shift thermal coefficient $\alpha$ (ppm/° C.) and constant intercept $\sigma0$ (ppm) were measured in 11 solutions with different NaCl concentrations (C=0.1, 1, 2, 5, 8, 11, 14, 17, 20, 23, 26% weight), by fitting the frequency shift f (ppm) of the maximum of the NMR peak versus 6 temperatures (T=25, 30, 35, 40, 45, 50° C.), for both the $^1H$ and $^{23}Na$ nuclei $$f=\alpha T+\sigma_0 \quad [13]$$

Effect of pH

In order to study the effect of pH on the multinuclear MR temperature measurements, solutions with different pH values were tested for $\Delta\alpha$ and $\Delta\sigma_0$ calibration. The solutions of different pH values were prepared by adding a small amount of acid HCl or base KOH solutions to the water solution sample with 1% weight NaCl, to adjust to the desired pH value. The pH was measured with a Fisher Scientific$^{PM}$ accumet$^{PM}$ AB150 pH Benchtop Meter and calibrated with three standard buffers with pH values 4.01, 7, and 10.01. The reported pH values were measured before acquiring the NMR data. The pH range was from 4.9 to 9.07. The results are summarized in FIG. 9 and demonstrate that pH has negligible influence on the $\Delta\alpha$ and $\Delta\sigma_0$ values.

Heating System and 1D CSI Procedure

An in-house built alternating-current resistive heating setup was constructed to create an NMR-compatible heating setup that does not interfere with the multinuclear NMR acquisition. A signal generator (B071HJ31WN, KKmoon, China), operating at 100 kHz was connected to a 130W class D amplifier (TPA3250D2EVM, Texas instruments Inc., USA). The output of the amplifier was connected to an in-house built low pass filter with a cutoff frequency of 10 MHz to mitigate RF waves being picked up and transmitted in close proximity to the RF coil in the NMR spectrometer. The output of the low pass filter was connected to a resistive wire insert made of wound AWG 32G enameled copper wire (ECW32AWG1LB, Bntechgo Inc., USA) placed inside the 5 mm NMR test tube filled with 2% agarose and 1% NaCl in water. A baseline proton 1D CSI acquisition was conducted with the following imaging parameters: 16 steps in the z-encoding, 1 average, and a repetition time of 15 s, giving a total experimental time of 5 min. A sodium 1D CSI acquisition over the same field of view was then acquired with the following parameters: 16 steps in the z-encoding, 32 averages, and a repetition time of 0.3 s, with a total experimental time of 5 min. The 1D CSI pulse sequence consisted of a 90° pulse followed by a pulsed gradient which encodes the spatial position in z-direction. After the baseline proton and sodium acquisitions were conducted, a 1V peak-to-peak sinusoidal waveform was used to drive the amplifier. The waveform at 100 kHz was used in order to not interfere with the RF, gradient or $B_0$ field. Sample temperature was monitored in real-time with the internal temperature probe of the Bruker 500 MHz spectrometer to ensure that heating of the sample was in a steady state. After twenty minutes, a steady-state of the temperature was attained, and CSI acquisitions were acquired at proton and sodium frequencies. Sodium and proton spectra were then used to reconstruct the absolute temperature. The absolute temperature was plotted and compared with IR temperature measurements acquired at steady-state temperature using a FLAIR IR camera (E75, FLIR Systems Inc., USA).

In short, the method comprises: 1) acquiring spectra or phase imaging using two nuclei or more, 2) reconstructing the phase or frequency of each nucleus, and 3) determining absolute thermometry from the frequency or phase difference between nuclei. In other words, a shift in phase or frequency for each nucleus is described as a function of temperature.

Although the examples describe the method involving a first nucleus and a second nucleus, the scope of the invention is not limited in this respect. Phase of frequency information for two or more nuclei (e.g., three nuclei, four nuclei, five nuclei, etc.) may be used to determine the absolute temperature of the sample. The spectra or phase imaging is acquired from at least one location within the sample (e.g., measurements for each nucleus may be taken at one location in the sample, measurements for each nucleus may be taken at two locations in the sample, measurements for each nucleus may be taken at three locations in the sample, etc.).

Although in many of the examples discussed below, the two or more nuclei are selected from the group of $^1H$, $^{23}Na$, $^{31}P$, $^{35}Cl$, $^{17}O$, $^6Li$, $^7Li$, or $^{39}K$, the scope of the invention is not limited in this respect. In other examples, nuclei other than $^1H$, $^{23}Na$, $^{31}P$, $^{35}Cl$, $^{17}O$, $^6Li$, $^7Li$, or $^{39}K$ may be used.

Results

Calibration of $\Delta\alpha$ and $\Delta\sigma_0$ in Solutions

The frequency shift thermal coefficient difference $\Delta\alpha$ and intercept difference $\Delta\sigma_0$ were measured in 11 samples with NaCl concentrations ranging from 0.1 to 26% (saturation) by weight. For each solution, NMR spectra were acquired at 6 different temperatures, as measured by the spectrometer sensor: 25, 30, 35, 40, 45, and 50° C. The corresponding real temperatures corrected using the spectrometer temperature calibration are shown in Table 2. The position of the peak maximum can follow a linear trend with temperature, with the slope corresponding to the frequency shift thermal coefficient $\alpha$, and the intercept $\sigma_0$. FIG. 1A shows examples of $^1H$ spectra at different temperatures. FIG. 1B shows examples of $^{23}Na$ spectra at different temperatures. The frequency changes with temperature are shown to vary with the NaCl concentration. The lineshapes appear broadened towards higher temperatures as a result of a slight temperature gradient across the sample, as well as probable heating of the shim coils that can alter the magnetic field in the volume of interest.

TABLE 2

| Spectrometer temperature calibration Temperature (° C.) | | | | | | |
|---|---|---|---|---|---|---|
| Theoretical (spectrometer) | 25 | 30 | 35 | 40 | 45 | 50 |
| Corrected (real) | 25.21 | 30.64 | 36.09 | 41.58 | 47.09 | 52.63 |

Figure 2B:
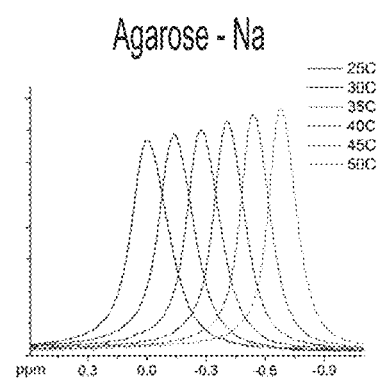
FIG. 2B shows sodium ($^{23}$Na) frequency shifts with temperature for an Agarose sample, according to an embodiment.
Figure 2C:
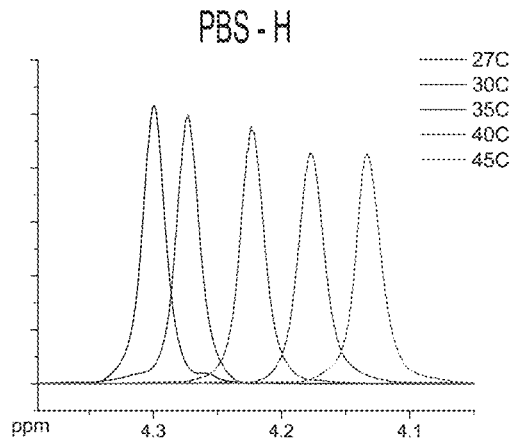
FIG. 2C shows hydrogen/proton ($^1$H) frequency shifts with temperature for a PBS sample, according to an embodiment.
Figure 2D:
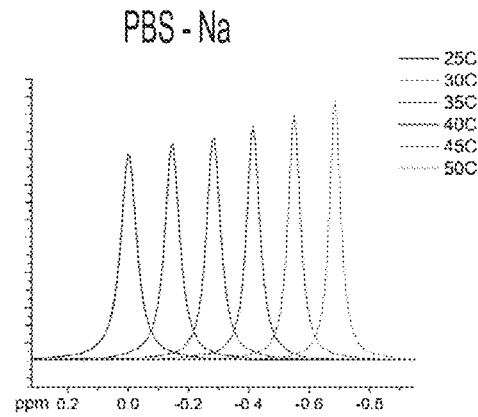
FIG. 2D shows sodium ($^{23}$Na) frequency shifts with temperature for a PBS sample, according to an embodiment.
Figure 2E:
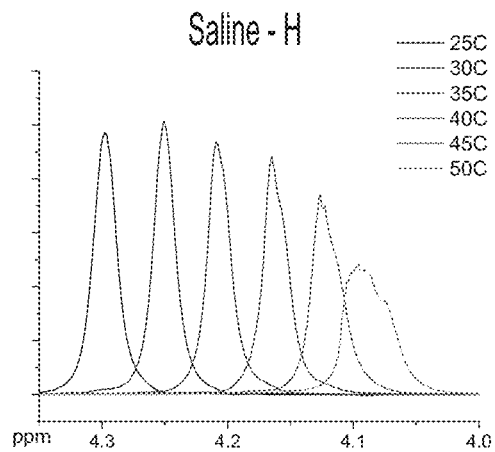
FIG. 2E shows hydrogen/proton ($^1$H) frequency shifts with temperature for a Saline sample, according to an embodiment.
Figure 2F:
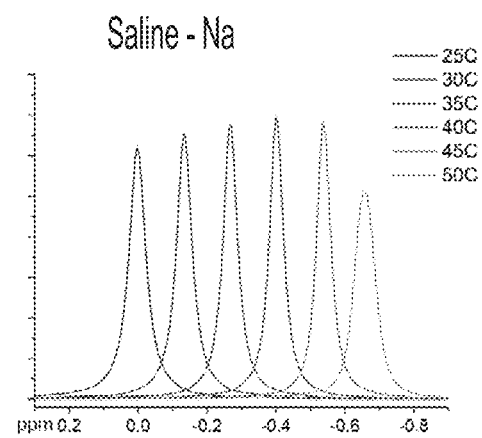
FIG. 2F shows sodium ($^{23}$Na) frequency shifts with temperature for a Saline sample, according to an embodiment.

FIG. 2A shows hydrogen/proton ($^1H$) frequency shifts with temperature for an Agarose sample. FIG. 2B shows sodium ($^{23}Na$) frequency shifts with temperature for an Agarose sample. FIG. 2C shows hydrogen/proton ($^1H$) frequency shifts with temperature for a PBS sample. FIG. 2D shows sodium ($^{23}Na$) frequency shifts with temperature for a PBS sample. FIG. 2E shows hydrogen/proton ($^1H$) frequency shifts with temperature for a Saline sample. FIG. 2F shows sodium ($^{23}Na$) frequency shifts with temperature for a Saline sample.

FIGS. 2G-2J show the results of the linear fitting of the frequency shift of $^1$H and sodium $^{23}$Na versus temperature for the 11 samples. Additionally, the figures show frequency shift thermal coefficients α (slope of the linear fit) and intercepts $\sigma_0$ (intercept of the linear fit) for $^1$H and $^{23}$Na, and their respective differences. The fits are shown in FIGS. 8A-8K. The frequency shift thermal coefficient α for $^1$H, shown in FIG. 2G, is consistent with literature, where the value of approximately −0.01 ppm/° C. is typically found for low NaCl concentrations (1% weight or less in biological tissues). The frequency shift thermal coefficient α for $^{23}$Na was approximately twice higher in magnitude than for $^1$H. The $^1$H and $^{23}$Na spectra for each sample were acquired on the same day at six temperatures, and the same shim was used for both nuclei. Different samples were acquired on different days in the following order: 1%, 26%, 11%, 17%, 23%, 8%, 0.1%, 2%, 5%, 14%, and 20%. This random order can ensure that the smooth variation that was detected for Δα and $\Delta\sigma_0$ with NaCl concentrations was not an effect of the spectrometer magnetic field drift or B$_0$ shim changes on different days. These variations of the magnetic field can, for example, be detected on individual $^1$H and $^{23}$Na measurements of $\sigma_0$ in FIG. 2I1. As shown on FIGS. 2I and 2J, both Δα and $\Delta\sigma_0$ showed a smooth variation with NaCl concentration, even when individual σ0 values for $^1$H and $^{23}$Na seem to fluctuate randomly in different samples acquired on different days. The variation of Δα is linear with increased NaCl concentration, while the variation of Δσ0 shows a nearly linear decrease with increasing NaCl concentration.

Effect of pH

Figure 9:
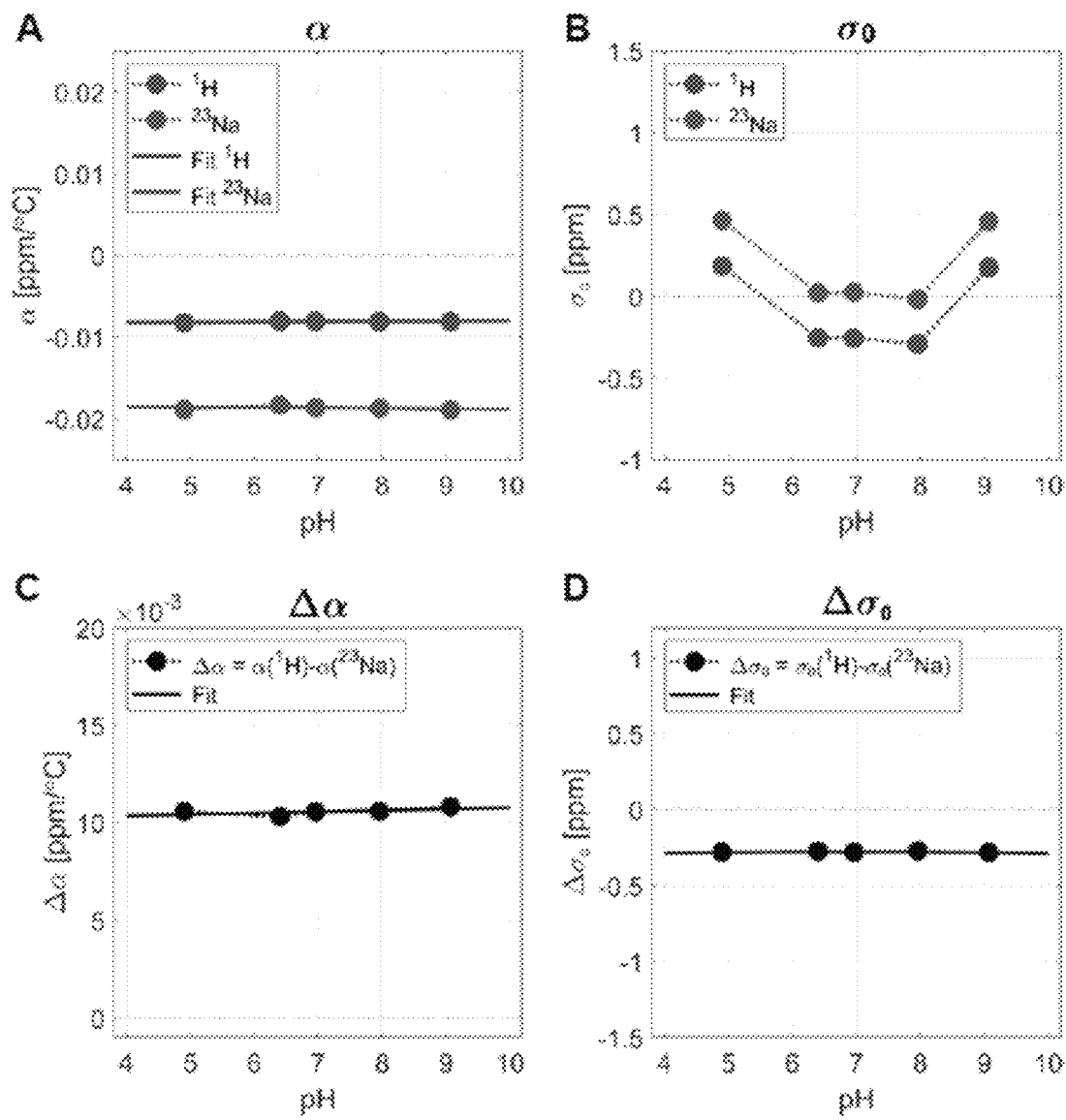
FIG. 9 shows a (ppm/° C.), $\sigma_0$ (ppm), $\Delta\alpha$ (ppm/° C.), and $\Delta\sigma_0$ (ppm) values for $^1$H and $^{23}$Na in a solution with 1% NaCl, for different pH, according to an embodiment.

Solutions with different pH values were tested for Δα and $\Delta\sigma_0$ calibration to study the effect of pH on the multinuclear MR temperature measurements. The pH range was from 4.9 to 9.07. The results are shown in FIG. 9. The pH can have a negligible influence on the Δα and $\Delta\sigma_0$ values.

Frequency Shifts with Temperature—Fits

Figure 3A:
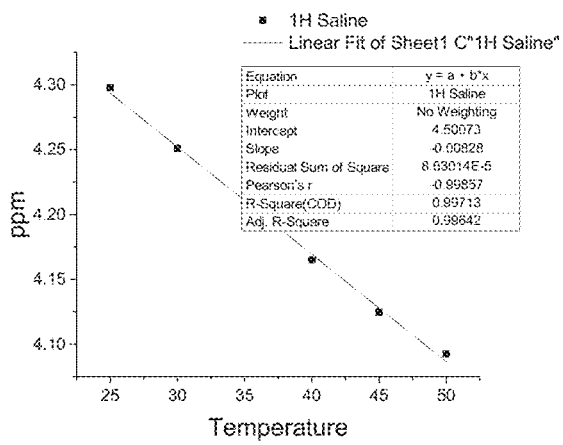
FIG. 3A shows a fit graph for a frequency shift with temperature for $^1$H in a Saline sample, according to an embodiment.
Figure 3B:
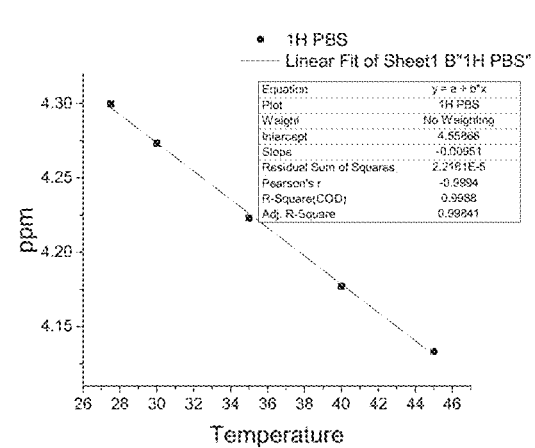
FIG. 3B shows a fit graph for a frequency shift with temperature for $^1$H in a PBS sample, according to an embodiment.
Figure 3C:
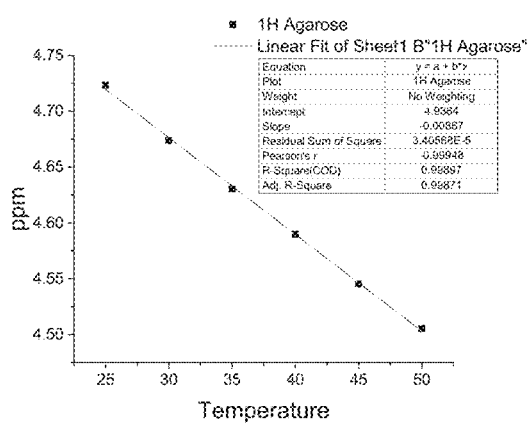
FIG. 3C shows a fit graph for a frequency shift with temperature for $^1$H in an Agarose sample, according to an embodiment.
Figure 3D:
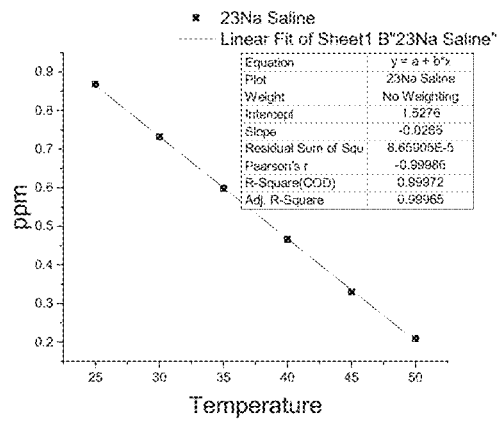
FIG. 3D shows a fit graph for a frequency shift with temperature for $^{23}$Na in a Saline sample, according to an embodiment.
Figure 3E:
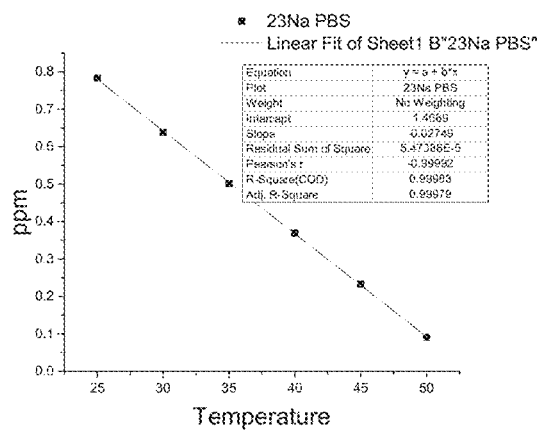
FIG. 3E shows a fit graph for a frequency shift with temperature for $^{23}$Na in a PBS sample, according to an embodiment.
Figure 3F:
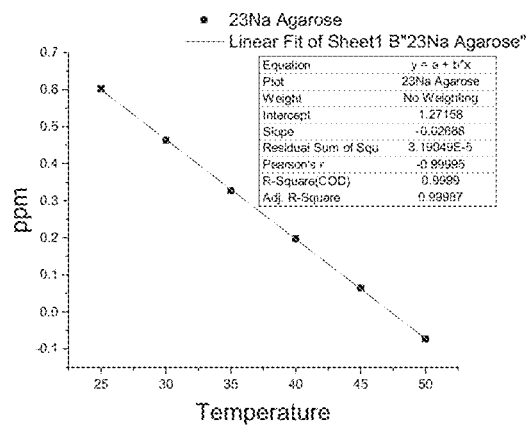
FIG. 3F shows a fit graph for a frequency shift with temperature for $^{23}$Na in an Agarose sample, according to an embodiment.

FIG. 3A shows a fit graph for a frequency shift with temperature for $^1$H in a Saline sample. FIG. 3B shows a fit graph for a frequency shift with temperature for $^1$H in a PBS sample. FIG. 3C shows a fit graph for a frequency shift with temperature for $^1$H in an Agarose sample. FIG. 3D shows a fit graph for a frequency shift with temperature for $^{23}$Na in a Saline sample. FIG. 3E shows a fit graph for a frequency shift with temperature for $^{23}$Na in a PBS sample. FIG. 3F shows a fit graph for a frequency shift with temperature for $^{23}$Na in an Agarose sample.

Blind Experiments in 1% NaCl Solution

Ten experiments were then carried out on a solution with NaCl concentration of 1% weight (similar to physiological conditions) to test the ability of the method to predict unknown temperatures. FIG. 3G shows the calculated temperatures for the data using the Δα and Δσ0 calibration obtained with the 1% solution used in FIGS. 2G-2I and Table 3. As a next step, three peak frequency measurements at 25° C., 30° C., and 40° C. were used to self-calibrate Δα and $\Delta\sigma_0$ for this sample, plotted by squares in FIG. 3H. The sample was then brought to three random blind temperatures with the same shimming conditions (diamonds in FIG. 3H). Then, the sample was brought to four more random blind temperatures where the magnet shims were randomly changed to alter B$_0$ (circles in FIG. 3H). Calculated temperatures in FIGS. 3G, 3H were in agreement with the reference temperatures ($R_{adj}^2$=0.998, RMSE ~0.34° C.). A similar experiment was conducted in a sample with 2% agarose and 1% NaCl. FIG. 3I shows the results of the calculated temperature plotted against the reference value using the pre-calibrated Δα and $\Delta\sigma_0$ from a 1% NaCl solution. In FIG. 3J, three frequency measurements were used to self-calibrate Δα and $\Delta\sigma_0$ in the gel itself, and three blind temperatures were calculated. In both cases, pre-calibration in a 1% NaCl solution and self-calibration in gel led to very similar results with accurate and precise measurement of the sample temperatures ($R_{adj}^2$=0.999, RMSE ~0.20° C.).

TABLE 3

Δα and $\Delta\sigma_0$ for different samples. Frequency shift thermal coefficient difference Δα = α($^1$H) − α($^{23}$Na) (in ppm/° C.), and intercept difference $\Delta\sigma_0 = \sigma_0(^1H) - \sigma_0(^{23}Na)$ (in ppm), were measured in different samples, either using self-calibration from the sample itself or pre-calibration from the solutions with 0.1-26% weight of NaCl.

| Samples | Calibration | Δα (ppm/° C.) | $\Delta\sigma_0$ (ppm) |
|---|---|---|---|
| Solution 1% | Solutions 0.1%-26% | 0.010690 | 0.056744 |
| Solution 1% | Self-calibration | 0.010301 | 0.070416 |
| Solution 0.3% | Solutions 0.1%-26% (fit) | 0.010720 | 0.075141 |
| Agarose | Self-calibration | 0.010321 | 0.075775 |
| Brain | Self-calibration | 0.011060 | 0.023918 |
| Muscle | Self-calibration | 0.011887 | −0.01556 |
| Kidney | Self-calibration | 0.011206 | 0.029343 |
| Liver | Self-calibration | 0.011500 | 0.034852 |

Figures 4A, 4B:
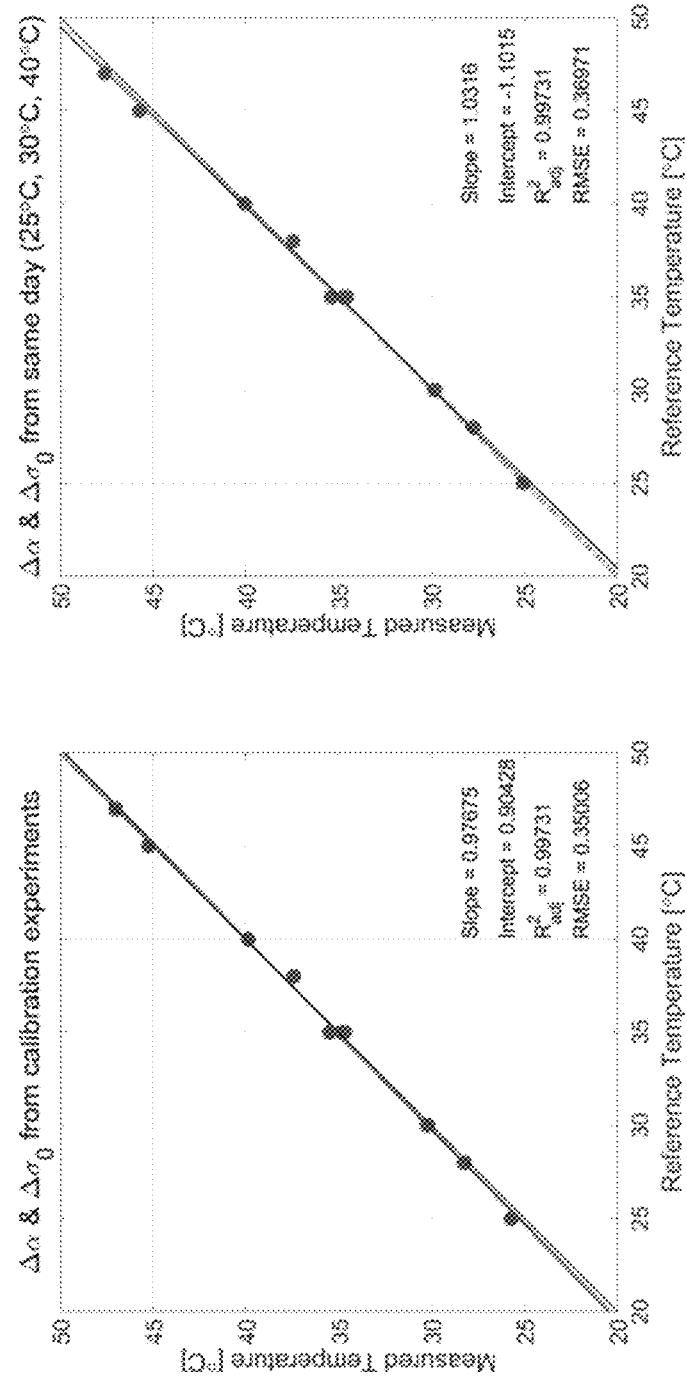
FIG. 4A shows a calibration of the absolute temperature model conducted on a water solution with 1% w/w NaCl at 25° C., 30° C., 35° C., 40° C., 45° C., 50° C. Via measurement of the frequency difference of the two nuclei, absolute temperature for three random temperatures were then predicted, according to an embodiment.
FIG. 4B shows the self-calibrated model version of FIG. 4A used for the prediction of temperature of a water solution with 1% w/w NaCl, according to an embodiment.

FIG. 4A shows a graph of predicted absolute temperature pre-calibrated experiments using 1% w/w NaCl solution calibration. The measurement was pre-calibrated with a different sample solution with 1% w/w NaCl in a previous experiment. FIG. 4B shows a graph generated by using data acquired at the temperatures at 25° C., 30° C. and 40° C. as references (for both $^{23}$Na and $^1$H) to calculate their respective α and $\sigma_0$, and their respective difference. Calibration was calculated using measurements at 25° C., 30° C., and 40° C. within the same sample and same experiment. The fitted temperature using a linear model with measurements taken at the same day and at different days (with different B$_0$ shims) were compared. Using conventional PRF absolute temperature would not be possible under different shims.

Figure 5:
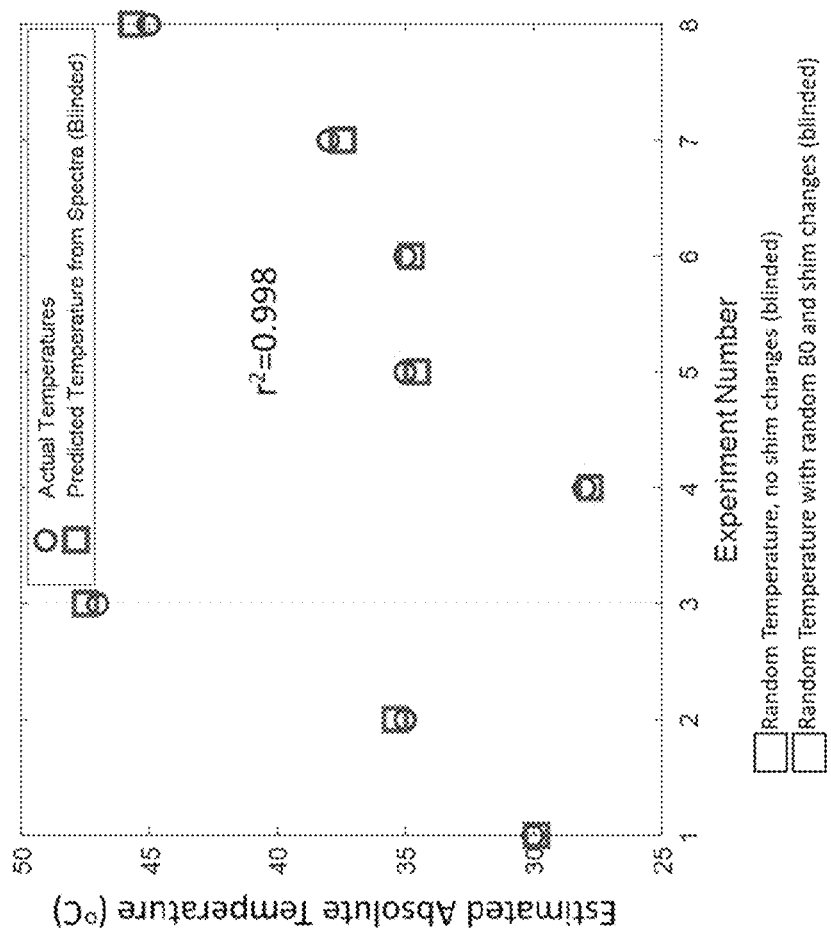
FIG. 5 shows the results of 8 experiments, according to an embodiment.

FIG. 5 shows the results of 11 experiments. First, three spectrum measurements at 25, 30 and 40° C. were used to calibrate the multi-nuclear thermometry model (not shown). The sample was then brought to three random temperatures. Lastly, the sample was brought to five more random temperatures (blinded) where the shim was randomly altered, changing the B$_0$ field. Actual and predicted temperature for the eight random temperatures are shown. Mean squared error (MSE)=0.18° C., showing robustness to B$_0$ shifts.

Referencing Signal to Detect Receive Chain Instabilities

One possible solution that can help reconstruction can be attained by having a "locked" frequency introduced by an external antenna placed in the scanner connected to a signal generator. These create a small-amplitude continuous wave near the resonant frequency of the proton and/or X-nuclei. In particular, the external antenna may be configured to transmit a signal at a predetermined frequency, which is detected and used to generate a reference frequency spectrum. This small peak would not affect the NMR signal integrity, but instead can provide a stable reference throughout the experiment. This reference signal can be used for calibration and to determine transmit/receive chain stability. If, for example, as seen in FIGS. 1A and 1B, a different frequency for each nucleus was observed relative to the reference peaks at the same temperature of sample, hardware instabilities may exist.

Affirmation of Temperature Smoothness

Spatial variation of temperature in the body occurs in a relatively-smooth manner. Thus, enforcing smoothness in the reconstruction may be used to better estimate the nuclei's screening coefficient or intramolecular screening coefficient. For example, when moving from one voxel to an adjacent one, a temperature gradient that is above a certain threshold can only be obtained by changing or updating the intramolecular or electrical screening coefficients.

Phase-Based Temperature Reconstruction

In one embodiment, the system and methods reconstruct temperature from independent phase maps. Prior techniques did not use the phase information to determine temperature. In contrast, described herein are methods that allow for reconstruction of temperature from phase information. The challenge is removing the electronic and $B_1$-related phase contributions, respectively. The measured phase for nucleus i, channel c and position r is given by:

$$\emptyset_{ic}(r, t) = \left[\frac{ref}{2\pi} - \frac{f_i(r, T)}{2\pi}\right]t + \emptyset_{c0} + \emptyset_{cB}(r) \quad [14]$$

where $\emptyset_{ic}(r,t)$ is the accumulated phase for nucleus i and channel c as a function of position r and acquisition time t. ref is the reference frequency (in Hz) at position r, $f_i(r,T)$ is the precession frequency (in Hz) as a function of position and temperature T, $\emptyset_{c0}$ is phase offset for the c-th channel, and $\emptyset_{cB}$ is the transmit- and receive-dependent phase change as a function of position.

The goal here is to estimate the approximate central frequency of the two or more nuclei from phase measurements acquired from gradient echo acquisitions (or other phase-sensitive acquisitions). Therefore, acquiring two phase measurements with different echo times (TE) gives:

$$\emptyset_{ic}(r, t)_{TE1} = \frac{ref}{2\pi}TE_1 - \frac{f_i(r, T)}{2\pi}TE_1 + \emptyset_{c0} + \emptyset_{cB}(r) \quad [15a]$$

$$\emptyset_{ic}(r, t)_{TE2} = \frac{ref}{2\pi}TE_2 - \frac{f_i(r, T)}{2\pi}TE_2 + \emptyset_{c0} + \emptyset_{cB}(r) \quad [15b]$$

Subtraction of [15a] and [15b] removes the phase offsets non-relating to $B_0$ give us:

$$\emptyset_{ic}(r, t)_{TE1} - \emptyset_{ic}(r, t)_{TE2} = \quad [16]$$
$$\frac{ref}{2\pi}TE_1 - \frac{fi(r, T)}{2\pi}TE_1 - \frac{ref}{2\pi}TE_2 + \frac{fi(r, T)}{2\pi}TE_2$$

Since the Ø's are measured, TEs and ref are known quantities, $f_i(r,T)$ can be estimated. Once $f_i(r,T)$ is quantified for each nucleus i, absolute temperature can be reconstructed by looking at the frequency difference between the two nuclei. It should be noted that, these subtraction measurements should be transmitter/receiver independent. Therefore, in multi-coil experiments the phase quantities from each channel can be summed to provide higher SNR.

Steps:

[1] Acquire images with different TEs for each nucleus i.

[2] With the phases solve the following equation to find $f_i(r,T)$:

$$\frac{2\pi\left[\emptyset_{ic}(r, t)_{TE1} - \emptyset_{ic}(r, t)_{TE2} + \frac{ref}{2\pi}TE_1 - \frac{ref}{2\pi}TE_2\right]}{[TE_2 - TE_1]} = f_i(r, T)$$

[3] Plug $f_i(r,T)$ for each nucleus A and B into step 1 of the spectroscopic method above and follow steps 2-4 to compute absolute temperature.

Ex Vivo Experiments

Figure 6A:
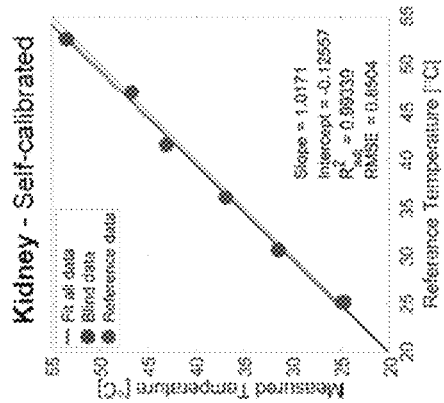
FIGS. 6A-6H show the temperatures measured in freshly excised ex vivo mouse tissues, according to an embodiment.
Figure 6B:
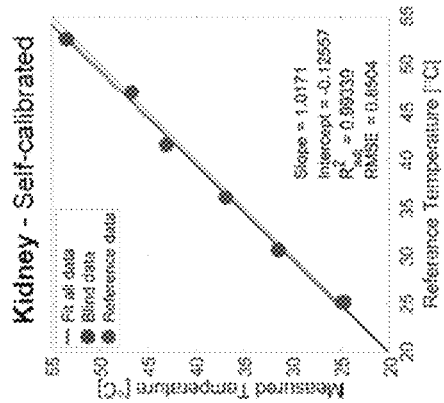
Figure 6C:
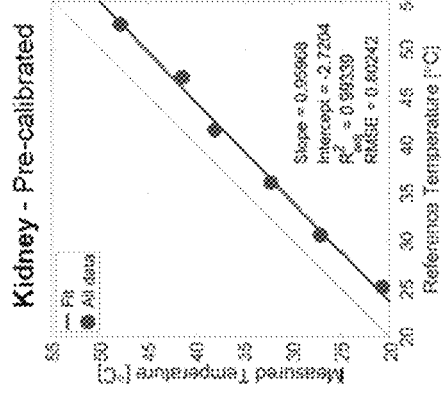
Figure 6D:
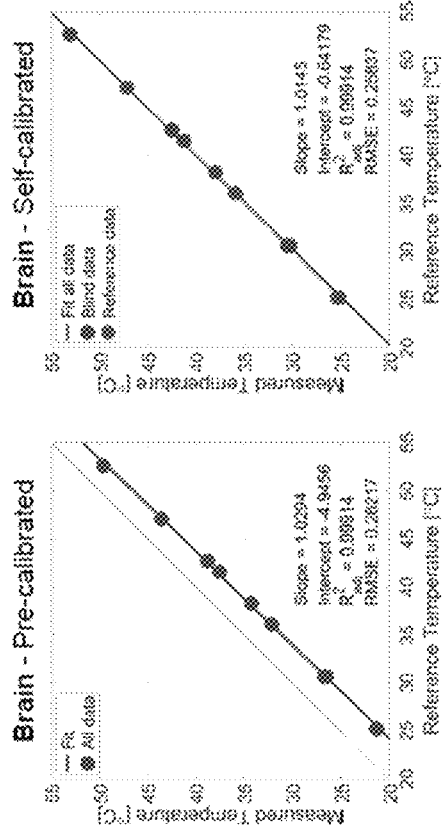
Figure 6E:
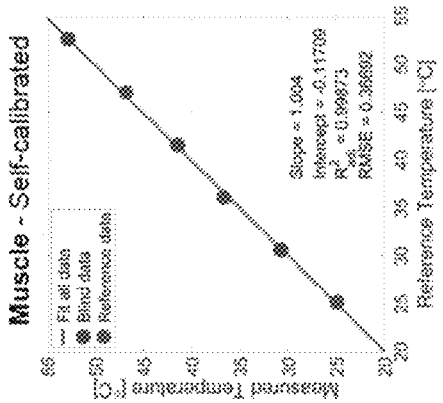
Figure 6F:
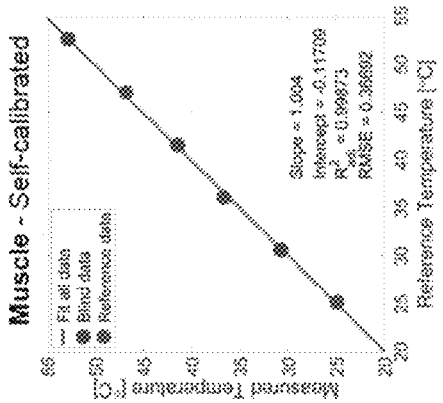
Figure 6G:
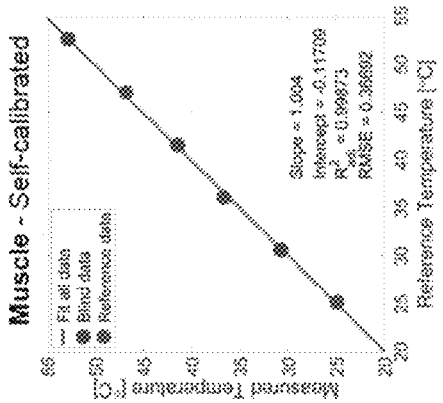
Figure 6H:
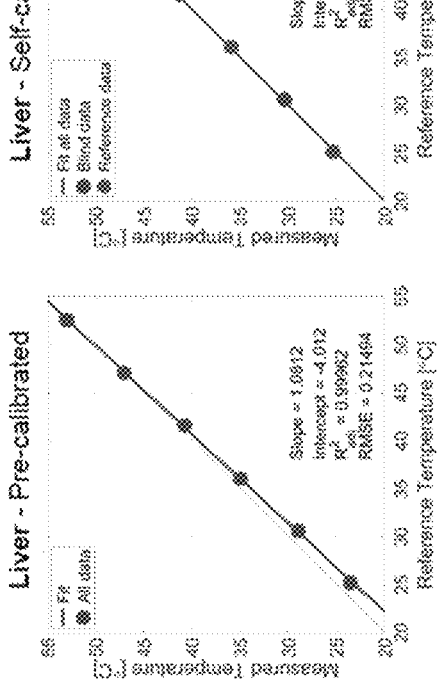

FIGS. 6A-6H show the temperatures measured in freshly excised ex vivo mouse tissues: brain in FIGS. 6A, 6B, kidney in FIGS. 6C, 6D, liver in FIGS. 6E, 6F, and muscle in FIGS. 6G, 6H. Three peak frequency measurements at 25° C., 35° C., and 45° C. were used for self-calibrating Δα and Δσ$_0$, and then other blind temperatures were calculated from this self-calibration. In the tissues, an excellent agreement was found for the calculated temperature when this self-calibration procedure was used, as shown in FIGS. 6A, 6C, 6E, and 6F. However, when the pre-calibration of Δα and Δσ$_0$ was calculated from a 0.3% NaCl solution (or approximately 50 mmol/L, similar to biological tissue concentrations) from fitting of the data measured at 0.1-26% NaCl, a constant offset of 1-5° C. is detected, depending on the tissues, as shown in FIGS. 6B, 6D, 6F, and 6H. Precalibration of Δα and Δσ$_0$ from the 1% NaCl and the 0.1% NaCl solution were also tested, with similar results than with 0.3% NaCl. In the case of liver, the pre-calibrated temperature measurement showed a good agreement with the reference temperature, as shown in FIG. 6E. A difference in sample preparation was that the consistency of the liver sample was still homogeneous when introduced in the NMR tube, while the other tissue samples were composed of small pieces, leading to a more inhomogeneous system which increased the susceptibility effects significantly (air bubbles, fat mixture within the tissue), resulting in a constant temperature offset.

1D CSI Experiment

Figures 7A, 7B, 7C:
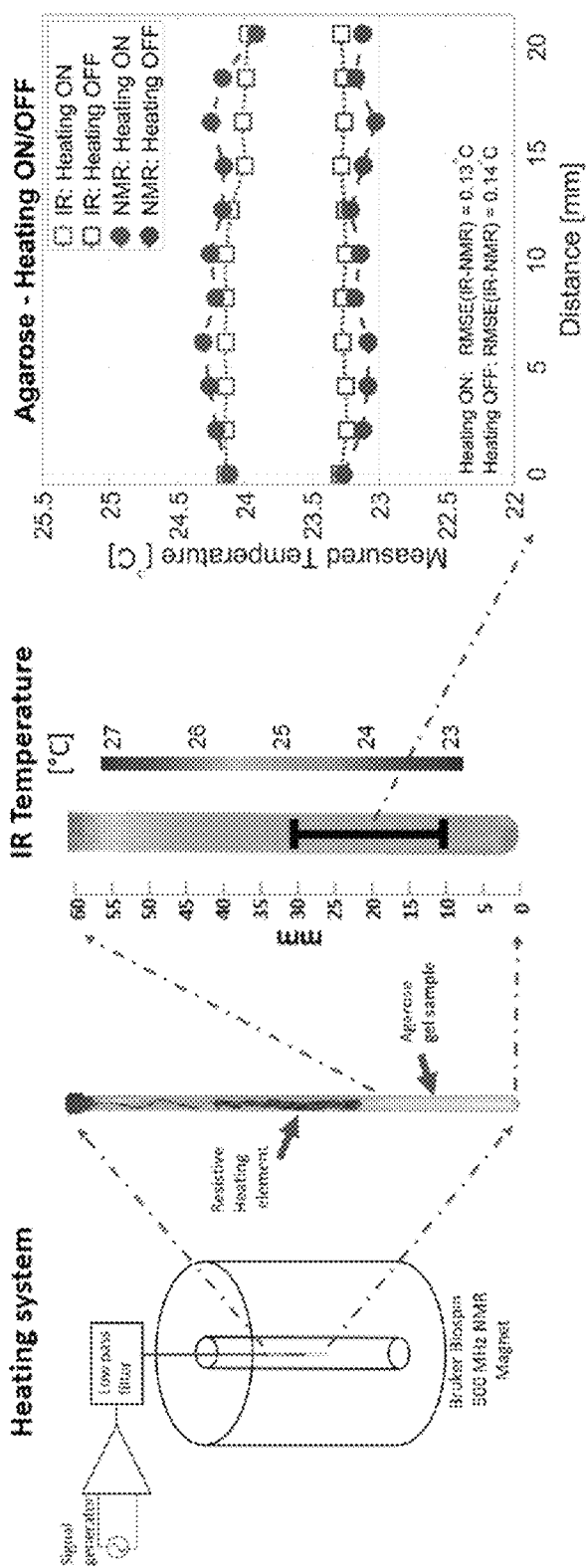
FIGS. 7A-7C show a comparison of 1D nuclear magnetic resonance (NMR) chemical shift imaging (CSI) results with infrared (IR) imaging in agarose, according to an embodiment.

To test the ability to map absolute temperature spatially, a 1D CSI measurement was carried out as shown in FIGS. 7A-7C. The experiment was conducted in the gel sample with 2% agarose and 1% NaCl. The heating system setup is shown in FIG. 7A and the spatial temperature map of the sample measured with an infrared (IR) camera is shown in FIG. 7B. FIG. 7C shows the measured temperatures using both IR camera (open square) and CSI data (closed circles) over 20 mm in the sample (NMR-detectable zone) before and after heating the sample. The measured temperatures using both methods are in good agreement, showing an increase of 1° C. along the entire sample after sample heating.

Possible Applications

This technique has wide applicability for: A) Improving monitoring and treatment of interventional work such as in the case of HIFU, RF ablation, RF hyperthermia, electroporation and more; B) Improving estimation of thermal damage using CEM43; C) Application of absolute thermometry as a biomarker for disease; D) utilization of absolute thermometry for thermal tissue property estimation; E) monitoring safety of MRI and/or Linac systems.

Brain Temperature

The brain comprises or roughly 2% of the human body mass, yet accounts for roughly 25% of the body's glucose consumption and 20% of oxygen consumption. It is the organ with the greatest metabolism and intense heat production. Temperature fluctuations intrinsically modulate behavioral changes and reflexively generate autonomic responses. Small and large animal studies have confirmed that temperature gradients of approximately 1 degree exist between cooler cortical regions to warmer basal regions and a rise and fall in temperature occurs with sleep and arousal. Temperature-dependence of cerebral functional activity has also been reported. In humans, on average brain temperature is less than 1° C. higher than the body temperature, unless injury impairs thermoregulation. For example, brain temperature in head trauma patients was shown to be on average 0.22° C. above body temperature. Similarly, in neurodegenerative diseases thermal regulation in the brain has been reported to be altered. Thus far the majority of studies measuring brain temperature were conducted using physical temperature probes placed inside the heads of animals. To this end, non-invasive accurate absolute thermometry is important for better understanding the complex thermoregulatory physiology of the human brain and as a biomarker for brain impairment/function.

Temperature in Cancer

The hallmark of malignant tumors is the tumors high metabolic activity and high blood perfusion. Recent studies have demonstrated localized temperature changes as a result of cancer activity. Thermographic imaging has been demonstrated on improving the evaluation of breast cancer by measurement of skin temperature adjacent to lesions. One of the biggest drawbacks of these techniques is the lack of ability to scan the internal microenvironment of the tumor. To this end, absolute multi-nuclear thermometry can assist in 3D evaluation of the tumor temperature relative to its environment.

Temperature in Inflammation

Tracing to the early 1900, experiments heating of inflamed tissue occur due to increased local biochemical activity of the cellular elements which participate in the inflammatory process. Inflammatory hyperemia, was found to be a physiological compensation for the abnormal local calorification. The rapid circulation of the blood in the inflamed part tends to moderate the increase in local temperature and to equalize the temperature with that of other parts of the body. To this end, absolute thermometry can be used to investigate in vivo inflammatory diseases/processes. For example, studies have suggested the presence of elevated temperature of the brain in patients with multiple sclerosis (MS). Elevated brain temperature was associated with worse fatigue in relapsing remitting patients. Better understanding and accurate temperature mapping can be used to improve monitoring and treatment of these patients.

CEM43

Heating of tissue is used for a wide variety of medical purposes ranging from treatment of cancer, ablation of tissue and more. The resulting temperature increase depends on the intensity and distribution of the energy delivered into the body and thermal properties of the tissue, e.g. permittivity, electrical conductivity, thermal conductivity, heat capacity and local blood perfusion. The cumulative equivalent minutes at 43° C. (CEM43° C.) model, as introduced by Sapareto and Dewey, is a concept that translates different temperature-time histories to a single number representing a "thermal dose." CEM43 has its roots in the direct cytotoxic effect of heat, whereby the amount of cell death depends on the temperature and exposure over time. Numerous prospective studies and studies with large patient numbers report thermal dose-effect relationships in various animal and human models. The CEM43 model describes only a single constant irreversible reaction of the total thermal damage process leading to loss of clonogenicity as a surrogate for cell death. Measurement of CEM43 in humans is currently impractical since absolute thermometry cannot be routinely conducted noninvasively inside the body. The multi-nuclear absolute MR thermometry method can enable in vivo CEM43 measurement.

Frequency Referencing (MRS, Protein NMR, etc.)

Frequency co-registration of two different nuclei in NMR can useful for better characterization of their microenvironment. Absolute frequency referencing is often desired in NMR and MRS. Frequency measurements on each nucleus can be done simultaneously and the relative position of one peak can be used for "locking" of the frequency of the other. Locking can be beneficial for removing changes in $B_0$ due to drift, motion, shim changes, susceptibility and more.

Discussion

A method of multi-nuclear absolute MR thermometry which takes advantage of the different and unique frequency shifts of the sodium and proton nuclei with temperature is disclosed. The method can be validated in fluid samples with different NaCl concentrations, in agarose gels, and in ex vivo fresh tissue from mice, with precise temperature control. Local magnetic field inhomogeneities can be a challenge for thermometry methods such as the PRF. The proposed multinuclear method can be shown to be less sensitive to $B_0$ inhomogeneities upon random shim variations.

Changes in water proton frequency shifts with temperature can reflect changes in the hydrogen-bonded structure of water. Two main models have been proposed to explain changes in water proton frequency shifts with temperature. In the first model, the temperature-induced frequency shift of water relates to the stretching and bending of the hydrogen bonds which are responsible for the electrical shielding effect. The second model describes a change in electrical shielding due to the breaking of the hydrogen bonds. Specifically, a steady state is created between ice-like lattice water structure, where hydrogen bonds are fully formed, and a monomeric water structure where no hydrogen bonds are present. These two models, when used independently, cannot fully explain the temperature- and ionic concentration-dependent frequency shift of water. Consequently, a mixed model where hydrogen bond length stretching and bending (model 1) alongside hydrogen bond rearrangements (model 2) can explain and predict experimental results on the temperature and ionic concentration dependency of the water frequency shift. The effect of strong electrolytes (such as NaCl) can cause a concentration-dependent shift in the proton resonance frequency, with some electrolytes inducing an increase in the frequency, while others, such as $Na^+$, inducing a reduction in the frequency. The chloride ion $Cl^-$ can have a small effect on the proton frequency shift relative to that of $Na^+$. When the sodium ion is surrounded by water, a hydration shell can be created, where, depending on the temperature, four to eight molecules of water can temporarily coordinate a single $Na^+$. In such solutions, water molecules can be in an unbound state with the ion (free water outside the hydration shell), which causes minimal change to the electrostatic structure of the hydrogen bond. For a fraction of time, water molecules can be in a bound state with the ion (hydration shell), causing a structural modification to the hydrogen bond, thus altering the electrical shielding of the $^1H$ nucleus. The time for which water is bound to the ion can be dependent on the NaCl concentration.

With respect to the frequency shift of the sodium ion, a strong correlation with the frequency shift of water can be observed, suggesting that a temperature-related modification of the hydrogen bonds coexists with a modification of the electrical shielding of the sodium ion. A temperature rise can increase the effective hydrogen bond length of water, increasing the negative charge distribution around the oxygen nucleus within the water molecule. This increase in negative charge distribution can intensify the ion-dipolar attraction between oxygen and sodium, consequently enhancing the electrical shielding of the sodium nucleus. As the concentration of NaCl increases, the magnitude of the frequency shift thermal coefficient α of sodium can decrease due to the competition between the ions for the water molecules, causing a decrease in average time for which water is bound to the ion. These effects form the basis for the multinuclear absolute thermometry method, enabling a sample-specific bijective mapping between the frequency difference of $^1$H and $^{23}$Na nuclei and temperature.

Once the proposed multinuclear thermometry method was calibrated on the aqueous solution with 1% NaCl, the frequency shift difference between the $^1$H and $^{23}$Na nuclei can be used to calculate the absolute temperature of the same sample under different shimming conditions with high accuracy (with an error of the order of 0.3° C. for temperatures between 25° C. and 50° C.). When calibration of the multinuclear thermometry method was conducted in aqueous solutions and then applied to predict the temperature in ex vivo tissue samples (brain, muscle, liver, and kidney), a constant temperature offset of 1-5° C. was observed. This offset can occur due to two main factors influencing the calibration of $\Delta\alpha$ and $\Delta\sigma_0$: (1) the preparation of the tissue samples, and (2) the presence of multiple ions inside the tissue samples. In case (1), the tissue samples were inserted in small pieces into the 5 mm NMR tubes, thus creating relatively inhomogeneous samples with air bubbles that are artificially inducing strong local susceptibility effects that are significantly stronger than under in vivo conditions. This tissue susceptibility was not present in the aqueous solution calibration of $\Delta\alpha$ and $\Delta\sigma_0$, and is most likely the main source of error. An exception was the liver sample that was kept uniform and homogeneous in the tube, hence a closer agreement between the pre-calibrated and the self-calibrated temperature measurements was found. In case (2), the presence of potassium ions $K^+$ can cause a proton frequency shift, while other ions generally induce smaller shifts due to their small chemical shift effect or their smaller concentrations in tissues. These ions were not present in the liquid samples, yet present in tissues at varying concentrations.

The volume of magnetic susceptibility can change linearly with temperature, and its effect on the $^1$H resonance frequency shift is roughly an order of magnitude smaller than the electrical shielding effect. As a result, calibration of the absolute thermometry method on the sample includes the sample-specific magnetic susceptibility shielding information for both sodium and proton. While susceptibility changes are accounted for in the model, measurement of temperature in voxels with very high susceptibility that alters the lineshapes of the spectra can be challenging since the reconstruction relies on detection of the proton and sodium spectra's center frequency. This effect was observed in our CSI measurements, where voxels close to the edge of the tube and close to the metallic resistive heating apparatus had to be excluded from the reconstruction due to spectral distortion.

The absolute temperature mapping method can be compatible with an implementation in vivo for potential medical applications, using either phase MRI or localized MRS at both the $^1$H and $^{23}$Na frequencies. Phase measurement acquisitions are more time-efficient than spectroscopic imaging as long repetition times needed to obtain high spectral resolution are not necessary, which can have an impact on the timing of clinical scanning. However, it is likely that translation of the proposed method to in vivo imaging can be challenging due to the low concentrations of sodium in vivo ranging between 15 and 150 mmol/L. These low concentrations combined with low $^{23}$Na NMR receptivity lead to low SNR and thus require low resolution (generally of the order of 4-6 mm isotropic) and long acquisition times (5-10 min) in MM experiments to compensate for the loss of signal. Line broadening that can be due to very short T2 relaxation in vivo (of the order of 1-15 ms), as well as potential anisotropy of the tissues, can make accurate sodium frequency estimation difficult. Moreover, MM systems with high magnetic fields (>3 T), and multi-channel dual-tuned dedicated RF coils (for brain, muscle or another organ of interest) can increase SNR and allow concomitant proton and sodium signals detection, which, in the short term, can limit the application of this method to research centers with these capabilities. Accuracy and precision of in vivo applications can also be strongly dependent on the precalibration of $\Delta\alpha$ and $\Delta\sigma_0$ for the two nuclei of interest ($^1$H and $^{23}$Na), that should probably be performed on a wide range of ex vivo tissue samples in order to minimize uncertainties in the temperature measurements. Lastly, even within the small range of sodium concentrations present in biological tissues and fluids (15-150 mmol/L, or about 0.1-1% weight), $\Delta\alpha$ and $\Delta\sigma_0$ can vary between tissues by about $4\times10^{-5}$ ppm/° C. and 0.02 ppm, respectively (according to the data acquired on solutions, see FIGS. 2G-2J), leading to uncertainties in accuracy of the temperature measurements of the order of 2° C. A potential solution would be to include the quantification of the tissue sodium concentration, using internal (cerebrospinal fluid, eyes) or external (gels, solutions) references, in the absolute MR thermometry protocol, and therefore correct $\Delta\alpha$ and $\Delta\sigma_0$ for each voxel of the image before temperature calculation, using for example extrapolation from the linear fits for low sodium concentrations (<1% wt) in FIGS. 2I and 2J. Translation and optimization of the multinuclear absolute thermometry technique to in vivo imaging, where both sodium and proton phase images can be acquired simultaneously or in an interleaved fashion can be studied.

A proof-of-concept general method for measuring the absolute temperature non-invasively in samples using a multinuclear magnetic resonance approach, based on the detection of the frequency shift difference between two different nuclei ($^1$H and $^{23}$Na in this case), and calibration of the difference of both their frequency shift thermal coefficients $\Delta\alpha$ (ppm/° C.) and constant intercepts $\Delta\sigma_0$ (ppm) is presented.

Spectrometer Temperature Calibration

The sample temperature was controlled with a variable temperature system, which is part of the Bruker spectrometer. The gas flow streams through a pipe along the sample tube and leaves the probe head at the top. A temperature sensor measures the temperature and gives the value to a control unit that regulates the heater power to keep the temperature constant. Since the temperature sensor is not inside the NMR tube, a calibration must be done in a sample with a known temperature-dependence behavior. Calibration data was previously acquired on this spectrometer on methanol, where the chemical shift difference between the peaks correlates to the real temperature. The range of temperatures was from −50° C. to 67° C. The real temperatures calculated from the frequency shifts of the peaks are compared to the temperatures obtained from the control unit in the spectrometer, and the following fitting parameters were obtained between the real temperature $T_{real}$ (° C.) in the sample and the temperature measured by the spectrometer sensor $T_{spec}$ (° C.):

$$T_{real} = a \cdot T_{spec}^2 + b \cdot T_{spec} + c \quad [14]$$

with $a = 5.944181 \times 10^4$, $b = 1.052388$, and $c = -1.470807$. The same correction is used for the experiments. Table 2 shows the resulting corrected (real) temperatures used in the experiments.

NaCl Concentration Calibration

The conversion of NaCl concentration C from % weight (% wt) unit to mol/L unit was calculated using the two following equations:

$$\rho = a \cdot C_{\%\ wt}^2 + b \cdot C_{\%\ wt} + c \quad [15]$$

with the density of water $\rho$ in kg/L or g/mL, $a = 1.682 \times 10^5$, $b = 0.007079$ and $c = 0.9984$, calculated using the data from the CRC Handbook of Chemistry and Physics (86th ed), p. 8-71, on the properties of water-NaCl mixtures (density of water at different NaCl concentrations in % wt); and $$C_{mol/L} = \frac{C_{\%wt}}{100} \times \frac{\rho}{M} \times 1000 \quad [16]$$

with M=58.44 g/mol the molar mass of NaCl. Results are presented in Table 1.

Uncertainty Calculation

Mass measurements were performed on a Mettler Toledo ME204E balance with a resolution of 0.1 mg according to the following method in order to decrease imprecision: (1) the balance was calibrated to zero before each measurement, (2) NaCl was added in very small amounts on the balance until the value measured increased by a step of 0.1 mg, and this until reaching the expected value for each sample. This method can thus be estimated to reasonably result in a measurement uncertainty of ±0.5 mg (or 0.1 mg uncertainty around the expected value). According to Equations [15] and [16], and standard error propagation, $$C_{mol/L} = \frac{10}{M} \times (a \cdot C_{\%wt}^3 + b \cdot C_{\%wt}^2 + c \cdot C_{\%wt}) \quad [17]$$

And the uncertainty $\sigma C_{mol/L}$ on $C_{mol/L}$ is:

$$\sigma C_{mol/L} = \quad [18]$$
$$\frac{\partial C_{mol/L}}{\partial C_{\%wt}} \times \sigma C_{\%wt} = \frac{10}{M} \times (3a \cdot C_{\%wt}^3 + 2b \cdot C_{\%wt}^2 + c \cdot C_{\%wt}) \times \sigma C_{\%wt}$$

with $\sigma C_{\%\ wt} = 0.05\%$ for $C_{\%\ wt} = 0.1\%$, and 0.5% for all other samples, according to the mass measurements for preparing samples and balance precision. Results are presented in Table 1.

Fitting of $\alpha$, $\Delta\alpha$, $\Delta\sigma_0$ vs. NaCl Concentrations

The values of $\alpha$ (ppm/° C.), and $\Delta\sigma$ (ppm/° C.), were measured at different NaCl concentrations $C_{\%\ wt}$ were fitted using the equations below. For $\alpha$ of $^1$H and $^{23}$Na, and for $\Delta\alpha$:

$$\alpha = a \cdot C_{\%\ wt} + b \quad [18a]$$

$$\Delta\alpha = a \cdot C_{\%\ wt} + b \quad [18b]$$

For $\Delta\sigma_0$:

$$\Delta\sigma_0 = a \cdot C_{\%\ wt}^2 + b \cdot C_{\%\ wt} + c \quad [19]$$

The fitting parameters are shown in FIG. 13.

Figure 8A:
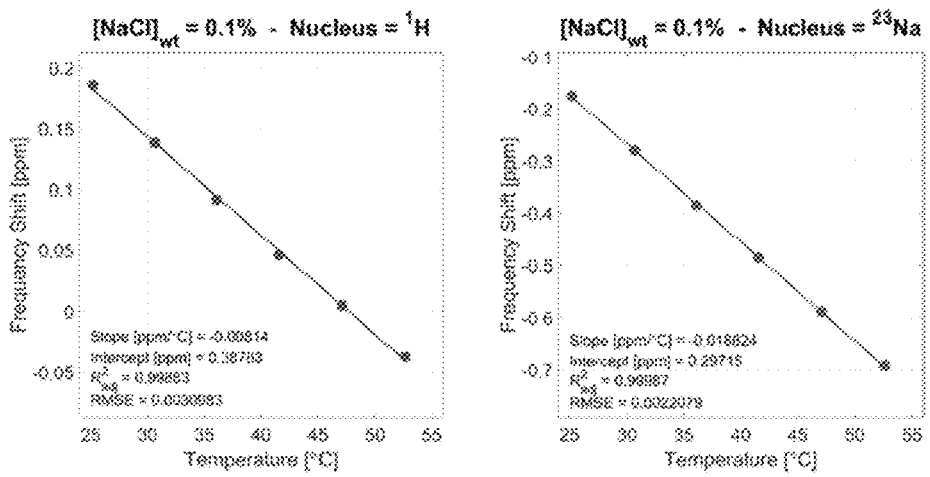
FIG. 8A shows proton ($^1$H) and sodium ($^{23}$Na) frequency shifts with temperature for a solution with [NaCl]=0.1% wt, according to an embodiment.
Figure 8B:
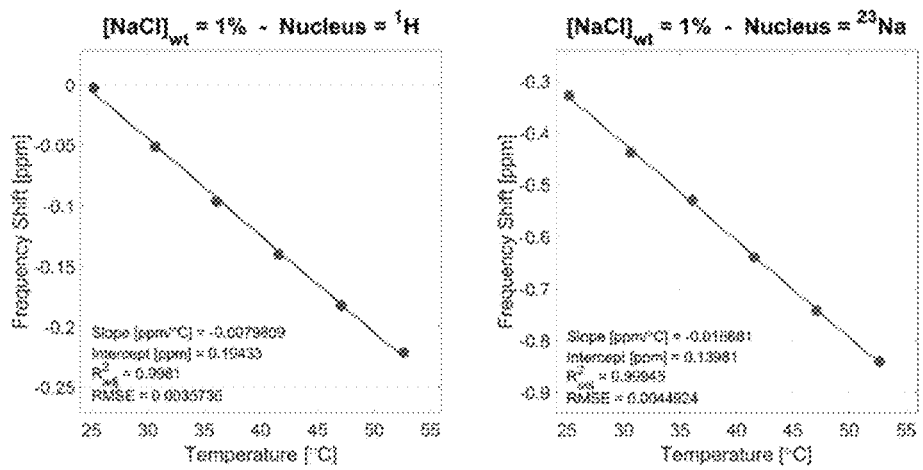
FIG. 8B shows proton ($^1$H) and sodium ($^{23}$Na) frequency shifts with temperature for a solution with [NaCl]=1% wt, according to an embodiment.
Figure 8C:
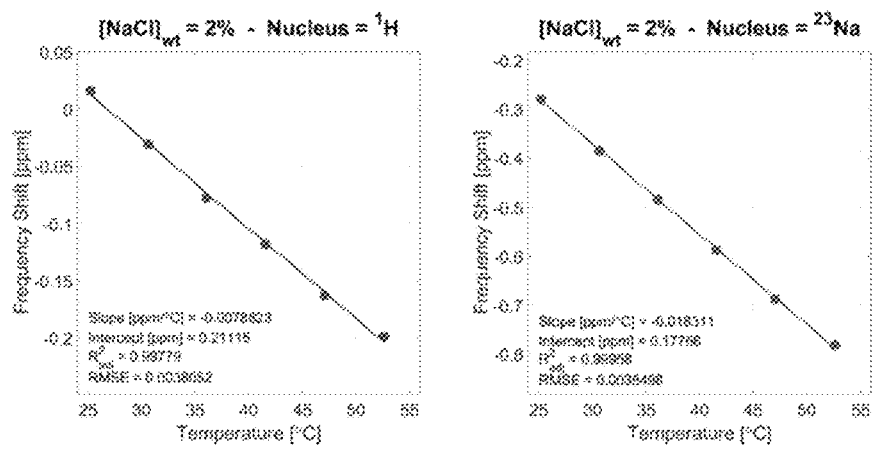
FIG. 8C shows proton ($^1$H) and sodium ($^{23}$Na) frequency shifts with temperature for a solution with [NaCl]=2% wt, according to an embodiment.
Figure 8D:
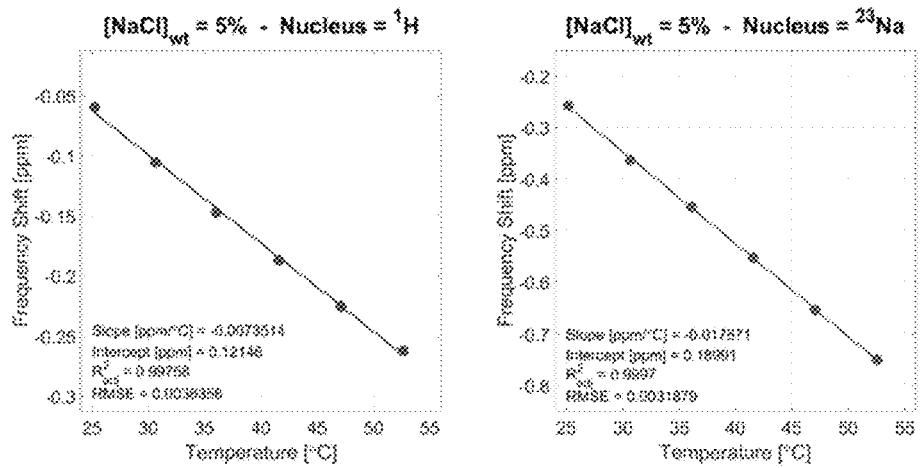
FIG. 8D shows proton ($^1$H) and sodium ($^{23}$Na) frequency shifts with temperature for a solution with [NaCl]=5% wt, according to an embodiment.
Figure 8E:
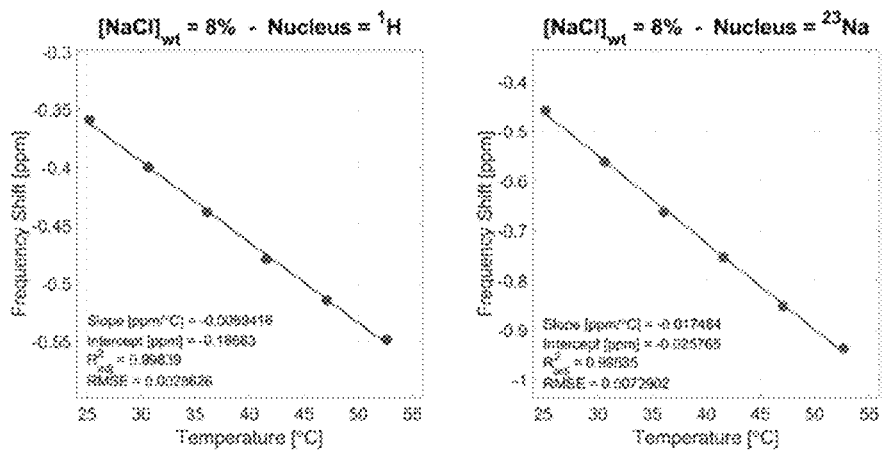
FIG. 8E shows proton ($^1$H) and sodium ($^{23}$Na) frequency shifts with temperature for a solution with [NaCl]=8% wt, according to an embodiment.
Figure 8F:
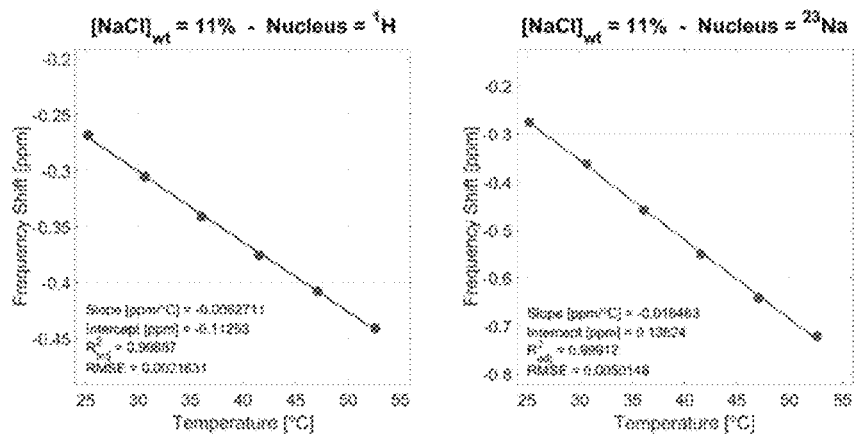
FIG. 8F shows proton ($^1$H) and sodium ($^{23}$Na) frequency shifts with temperature for a solution with [NaCl]=11% wt, according to an embodiment.
Figure 8G:
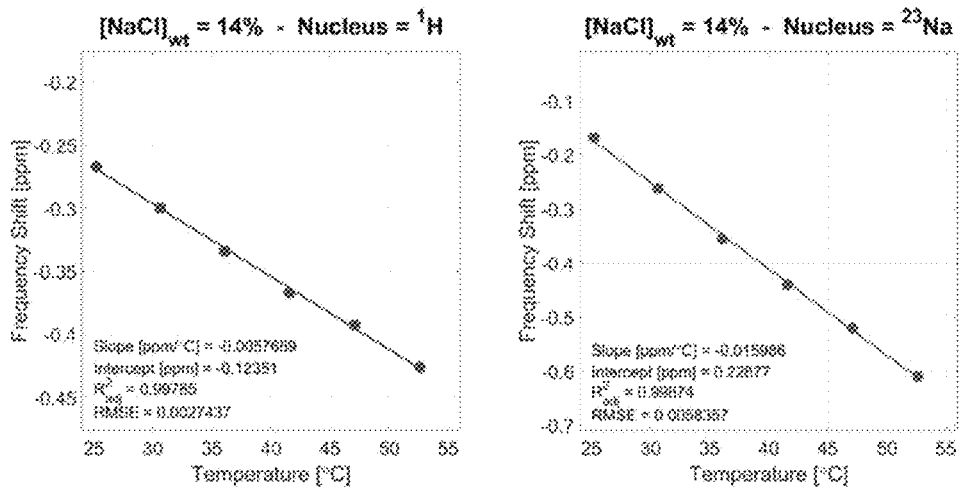
FIG. 8G shows proton ($^1$H) and sodium ($^{23}$Na) frequency shifts with temperature for a solution with [NaCl]=14% wt, according to an embodiment.
Figure 8H:
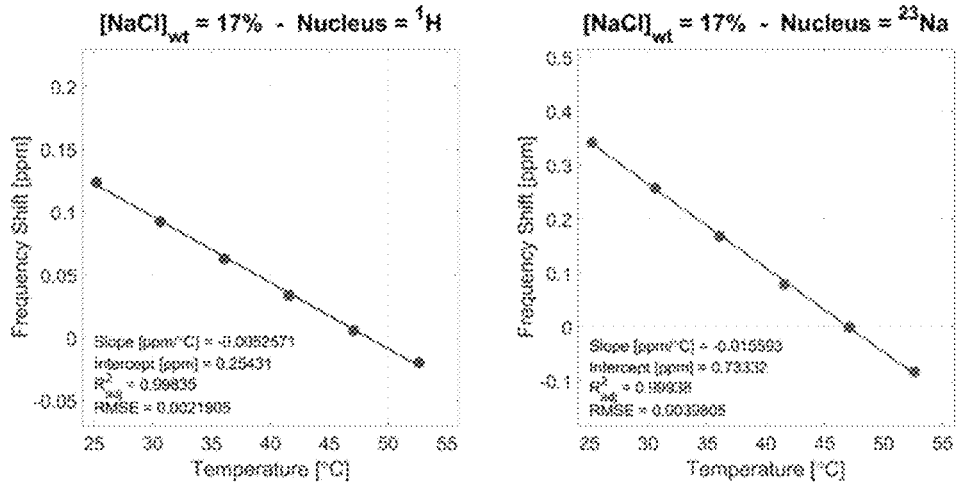
FIG. 8H shows proton ($^1$H) and sodium ($^{23}$Na) frequency shifts with temperature for a solution with [NaCl]=17% wt, according to an embodiment.
Figure 8I:
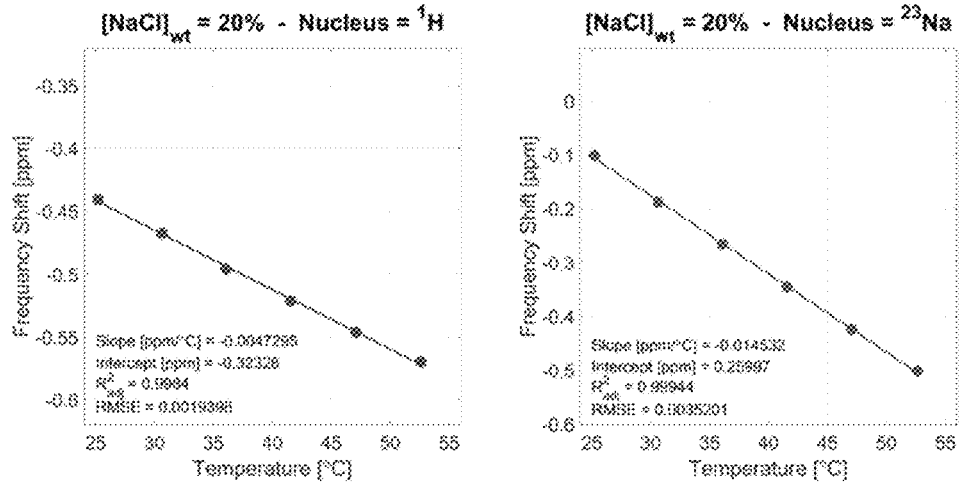
FIG. 8I shows proton ($^1$H) and sodium ($^{23}$Na) frequency shifts with temperature for a solution with [NaCl]=20% wt, according to an embodiment.
Figure 8J:
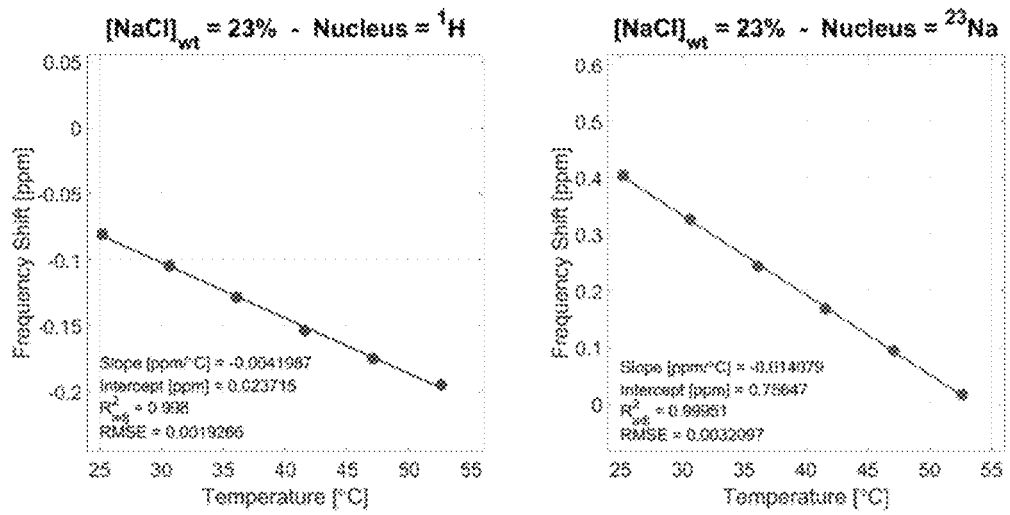
FIG. 8J shows proton ($^1$H) and sodium ($^{23}$Na) frequency shifts with temperature for a solution with [NaCl]=23% wt, according to an embodiment.
Figure 8K:
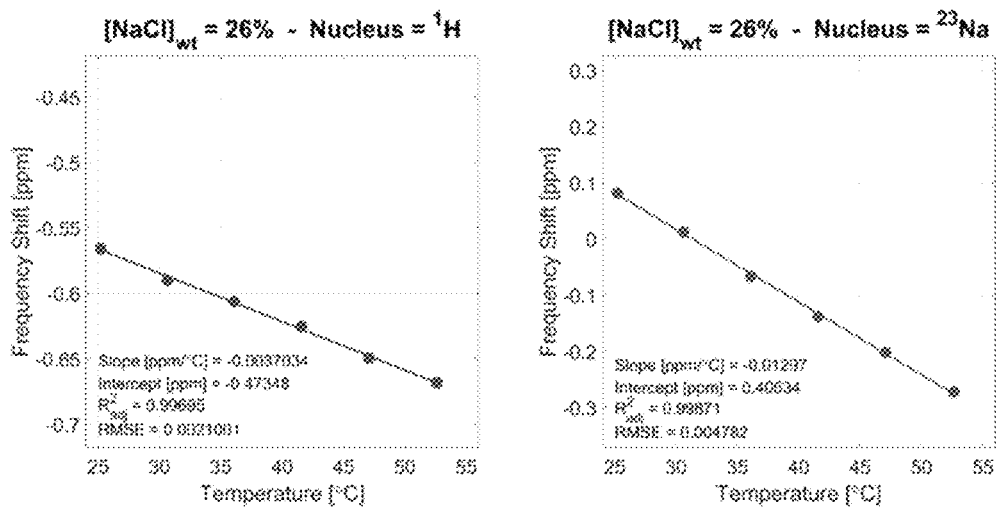
FIG. 8K shows proton ($^1$H) and sodium ($^{23}$Na) frequency shifts with temperature for a solution with [NaCl]=26% wt, according to an embodiment.

FIG. 8A shows proton ($^1$H) and sodium ($^{23}$Na) frequency shifts with temperature for a solution with [NaCl]=0.1% wt.
FIG. 8B shows proton ($^1$H) and sodium ($^{23}$Na) frequency shifts with temperature for a solution with [NaCl]=1% wt.
FIG. 8C shows proton ($^1$H) and sodium ($^{23}$Na) frequency shifts with temperature for a solution with [NaCl]=2% wt.
FIG. 8D shows proton ($^1$H) and sodium ($^{23}$Na) frequency shifts with temperature for a solution with [NaCl]=5% wt.
FIG. 8E shows proton ($^1$H) and sodium ($^{23}$Na) frequency shifts with temperature for a solution with [NaCl]=8% wt.
FIG. 8F shows proton ($^1$H) and sodium ($^{23}$Na) frequency shifts with temperature for a solution with [NaCl]=11% wt.
FIG. 8G shows proton ($^1$H) and sodium ($^{23}$Na) frequency shifts with temperature for a solution with [NaCl]=14% wt.
FIG. 8H shows proton ($^1$H) and sodium ($^{23}$Na) frequency shifts with temperature for a solution with [NaCl]=17% wt.
FIG. 8I shows proton ($^1$H) and sodium ($^{23}$Na) frequency shifts with temperature for a solution with [NaCl]=20% wt.
FIG. 8J shows proton ($^1$H) and sodium ($^{23}$Na) frequency shifts with temperature for a solution with [NaCl]=23% wt.
FIG. 8K shows proton ($^1$H) and sodium ($^{23}$Na) frequency shifts with temperature for a solution with [NaCl]=26% wt.

FIG. 9 shows $\alpha$ (ppm/° C.), $\sigma_0$ (ppm), $\Delta\alpha$ (ppm/° C.), and $\Delta\sigma_0$ (ppm) values for $^1$H and $^{23}$Na in a solution with 1% NaCl, for different pH.

FIG. 10 shows examples of single Lorentzian fitting of 256+1 data points around the maximum of the $^1$H and $^{23}$Na spectra at different temperatures for the muscle tissue sample. Fit curves are solid (thick) lines and original data appear as linked data points (thin lines).

FIG. 11 shows examples of bi-Lorentzian fitting of full $^1$H and $^{23}$Na spectra at 3 different temperatures for the muscle tissue. Fit curves are thick solid lines, original data are linked data points, and residuals between data and fit are in dashed lines.

FIG. 12 shows linear fits of frequency shift f vs. temperature T: $f = \alpha T + \sigma_0$.

FIG. 13 shows fitting parameters for a, $\Delta\alpha$, $\Delta\sigma_0$ versus NaCl concentrations in weight % ($C_{\%\ wt}$).

Figure 14:
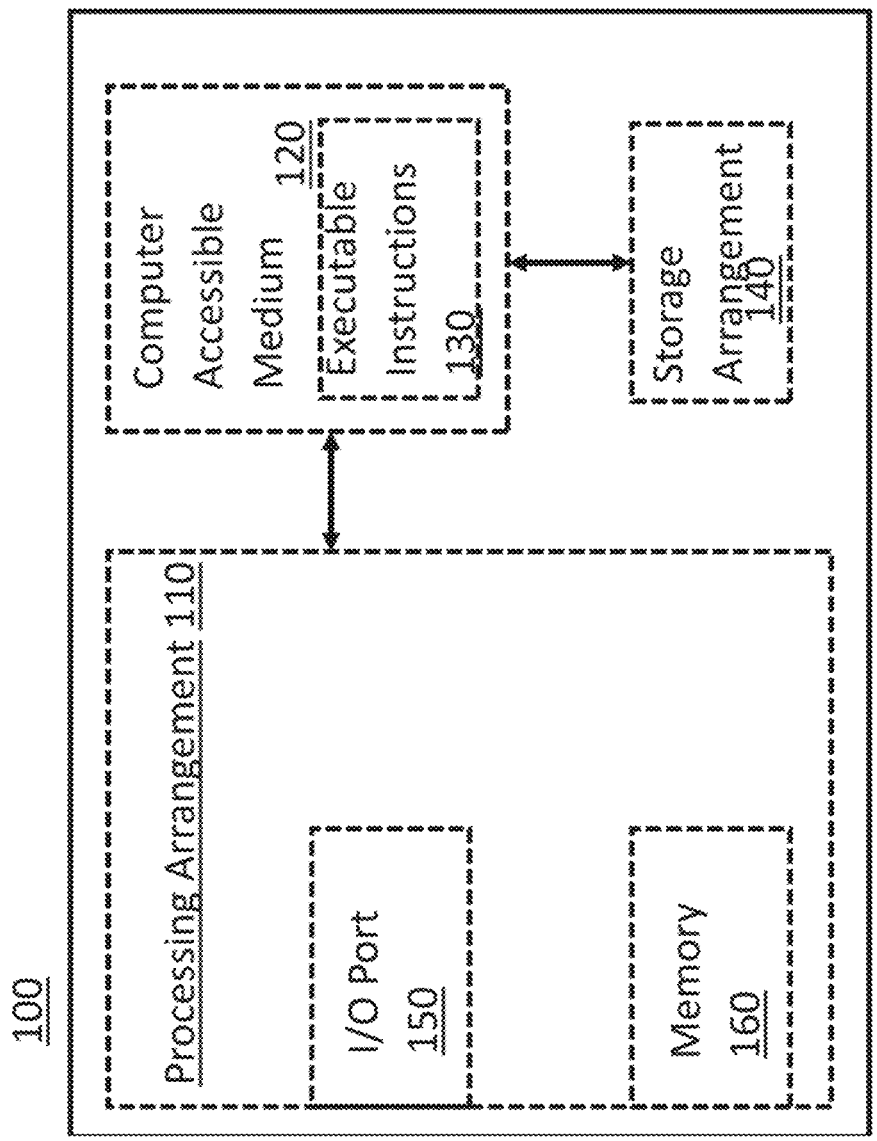
FIG. 14 illustrates a computer system for use with certain implementations, according to an embodiment.

As shown in FIG. 14, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The processing arrangement 110 can include an I/O port 150. The processing arrangement 110 can include memory 160. The computer-accessible medium 120 may be a non-transitory computer-accessible medium. The computer-accessible medium 120 can contain executable instructions 130 thereon. In addition, or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions. For example, in some implementations, the instructions may include instructions for applying radio frequency energy in a plurality of sequence blocks to a volume, where each of the sequence blocks includes at least a first stage. The instructions may further include instructions for repeating the first stage successively until magnetization at a beginning of each of the sequence blocks is stable, instructions for concatenating a plurality of imaging segments, which correspond to the plurality of sequence blocks, into a single continuous imaging segment, and instructions for encoding at least one relaxation parameter into the single continuous imaging segment.

System 100 may also include a display or output device, an input device such as a keyboard, mouse, touch screen or other input devices, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled", "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A computer-implemented machine for reconstruction of absolute temperature of a sample, comprising:
    a processor; and
    a tangible computer-readable medium operatively connected to the processor and including computer code configured to:
        determine a frequency for a first nucleus at at least one location in the sample;
        determine a second frequency for a second nucleus at the at least one location in the sample;
        normalize the frequency for the first nucleus with a first intramolecular shielding constant to obtain normalized frequency information for the first nucleus;
        normalize the frequency for the second nucleus with a second intramolecular shielding constant to obtain normalized frequency information for the second nucleus; and
        determine an absolute temperature of the sample based on a difference between the normalized frequency information for the first nucleus and the normalized frequency information for the second nucleus,
        wherein the first nucleus and the second nucleus are different elements.

2. The computer-implemented machine of claim 1, wherein the first nucleus and the second nucleus are different elements selected from the group consisting of $^{1}$H, $^{23}$Na, $^{31}$P, $^{35}$Cl, $^{17}$O, $^{6}$Li, $^{7}$Li, and $^{39}$K.

3. The computer-implemented machine of claim 1, further comprising computer code configured to determine electrical shielding information for the first nucleus, wherein the electrical shielding information comprises an indication of a degree to which an electron density around the first nucleus shields the first nucleus from an external magnetic field.

4. The computer-implemented machine of claim 1, further comprising computer code configured to determine electrical shielding information for the second nucleus, wherein the electrical shielding information comprises an indication of a degree to which an electron density around the second nucleus shields the second nucleus from an external magnetic field.

5. The computer-implemented machine of claim 1, wherein the sample comprises tissue or an organ.

6. The computer-implemented machine of claim 5, wherein
the sample comprises brain tissue or a brain, and
the computer code is configured to determine a biomarker for brain function based upon the absolute temperature of the brain tissue or the brain.

7. The computer-implemented machine of claim 1, wherein
the sample comprises a tumor, and
the computer code is configured to determine the absolute temperature of the tumor.

8. The computer-implemented machine of claim 1, wherein the computer code is configured to determine the absolute temperature of the sample as a biomarker for biochemical activity of an inflamed tissue.

9. The computer-implemented machine of claim 1, wherein the computer code is configured to reconstruct the absolute temperature from phase information.

10. A method for reconstruction of absolute temperature of a sample, comprising:
determining a frequency for a first nucleus at at least one location in the sample;
determining a frequency for a second nucleus at the at least one location in the sample;
normalizing the frequency for the first nucleus with a first intramolecular shielding constant to obtain normalized frequency information for the first nucleus;
normalizing the frequency for the second nucleus with a second intramolecular shielding constant to obtain normalized frequency information for the second nucleus; and
determining an absolute temperature of the sample based on a difference between the normalized frequency information for the first nucleus and the normalized frequency information for the second nucleus,
wherein the first nucleus and the second nucleus are different elements.

11. The method of claim 10, wherein the first nucleus and the second nucleus are different elements selected from the group consisting of $^{1}$H, $^{23}$Na, $^{31}$P, $^{35}$Cl, $^{17}$O, $^{6}$Li, $^{7}$Li, or $^{39}$K.

12. The method of claim 10, further comprising:
determining a frequency for at least one additional nucleus at the at least one location in the sample; and
normalizing the frequency for the at least one additional nucleus with a respective intramolecular shielding constant for each additional nucleus to obtain normalized frequency information for each additional nucleus;
wherein determining the absolute temperature of the sample is based on a difference between the normalized frequency information for the first nucleus, the normalized frequency information for the second nucleus, and the normalized frequency for the at least one additional nucleus, and
wherein the first nucleus, the second nucleus, and the at least one additional nucleus are different elements.

13. A method for reconstruction of absolute temperature of a sample, comprising:
acquiring spectra directly from MR spectroscopy from a first nucleus and a second nucleus different from the first nucleus, the first nucleus and the second nucleus being present in the sample;
reconstructing frequency information for the first nucleus and frequency information for the second nucleus; and
determining an absolute temperature of the sample based on a difference between the frequency information for the first nucleus and the frequency information for the second nucleus,
wherein the first nucleus and the second nucleus are different elements selected from the group consisting of $^{1}$H, $^{23}$Na, $^{31}$P, $^{35}$Cl, $^{17}$O, $^{6}$Li, $^{7}$Li, or $^{39}$K.

14. The method of claim 13, wherein the frequency information for the first nucleus and the frequency information for the second nucleus comprise a precession frequency.

15. The method of claim 13, further comprising determining electrical shielding information for the first nucleus, wherein the electrical shielding information comprises an indication of a degree to which an electron density around the first nucleus shields the first nucleus from an external magnetic field.

16. The method of claim 13, further comprising determining electrical shielding information for the second nucleus, wherein the electrical shielding information comprises an indication of a degree to which an electron density around the second nucleus shields the second nucleus from an external magnetic field.

17. The method of claim 13, wherein the sample comprises a tissue, an organ, or a tumor.

18. The method of claim 17, wherein the sample comprises brain tissue or a brain, and the method further comprises determining a biomarker for brain function based upon the absolute temperature of the brain tissue or the brain.

19. The method of claim 13, wherein the sample comprises a tissue, and the method further comprises determining a biomarker for biochemical activity of an inflamed tissue based on the absolute temperature of the tissue.

20. The method of claim 13, wherein the sample comprises a tissue or an organ, and the method further comprises determining the absolute temperature of the tissue or organ during thermal ablation of the tissue or organ at a cumulative equivalent minute at 43° C. (CEM43).

* * * * *